(12) United States Patent  (10) Patent No.: US 9,072,520 B2
Terada  (45) Date of Patent: Jul. 7, 2015

(54) CLIP UNIT AND LIGATION DEVICE USING THE SAME

(75) Inventor: Kazuhiro Terada, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 274 days.

(21) Appl. No.: 13/598,420

(22) Filed: Aug. 29, 2012

(65) Prior Publication Data

US 2013/0072945 A1  Mar. 21, 2013

(30) Foreign Application Priority Data

Sep. 15, 2011  (JP) ................. 2011-202024

(51) Int. Cl.
*A61B 17/122* (2006.01)
*A61B 17/128* (2006.01)
*A61B 17/00* (2006.01)
*A61B 17/29* (2006.01)

(52) U.S. Cl.
CPC ... *A61B 17/1227* (2013.01); *A61B 2017/00584* (2013.01); *A61B 17/1222* (2013.01); *A61B 17/1285* (2013.01); *A61B 2017/2901* (2013.01); *A61B 2017/2911* (2013.01)

(58) Field of Classification Search
CPC .. A61B 17/0487; A61B 17/068; A61B 17/08; A61B 17/083; A61B 17/10; A61B 17/122; A61B 17/1227; A61B 17/128; A61B 17/1285; A61B 2017/0488; A61B 2017/00584

USPC ................. 606/139, 142, 143, 151, 157, 158; 623/23.72

See application file for complete search history.

(56) References Cited

U.S. PATENT DOCUMENTS

| 3,958,576 | A  | * | 5/1976  | Komiya ................... 606/142 |
| 2002/0045909 | A1 |   | 4/2002  | Kimura et al. |
| 2005/0107809 | A1 | * | 5/2005  | Litscher et al. ........... 606/142 |
| 2007/0112359 | A1 | * | 5/2007  | Kimura et al. ............ 606/142 |
| 2008/0027467 | A1 |   | 1/2008  | Satake et al. |
| 2009/0326558 | A1 | * | 12/2009 | Cui et al. .................. 606/143 |
| 2010/0036396 | A1 | * | 2/2010  | Iida et al. ................. 606/143 |

FOREIGN PATENT DOCUMENTS

JP  4116049 B2  7/2008
JP  4472719 B2  6/2010

* cited by examiner

*Primary Examiner* — Ryan Severson
*Assistant Examiner* — Rachel S Papeika
(74) *Attorney, Agent, or Firm* — McGinn IP Law Group, PLLC

(57) ABSTRACT

A clip unit for ligating a biological body includes: a clip body having a pair of arm parts; and a fastening ring arranged in an outside of the clip body, and configured to fasten the arm parts, in which: the fastening ring includes a flap part configured to expand diametrically outward from the fastening ring, and a flap retaining unit configured to retaining an expansion extent of the flap part at a given extent.

15 Claims, 43 Drawing Sheets

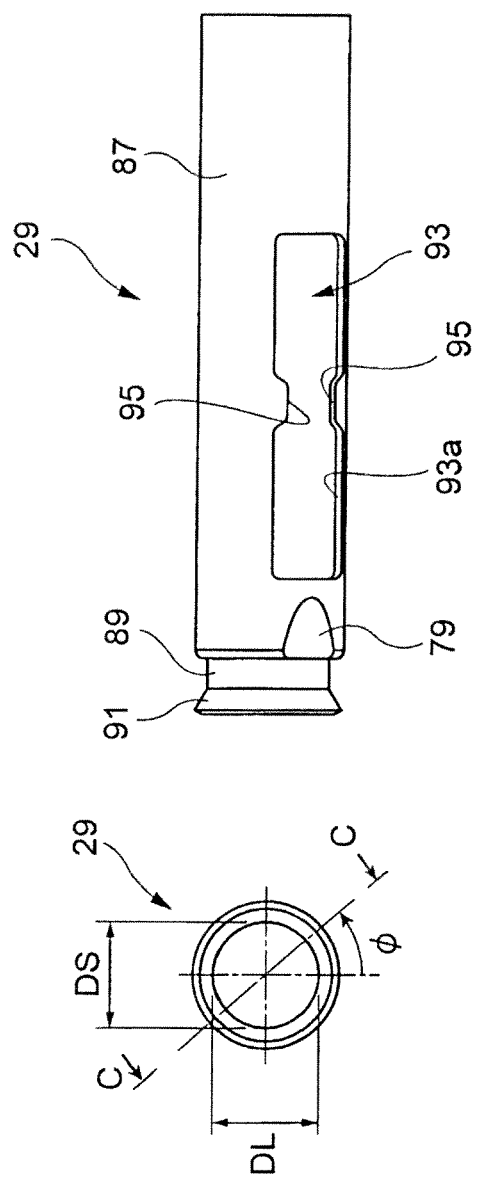

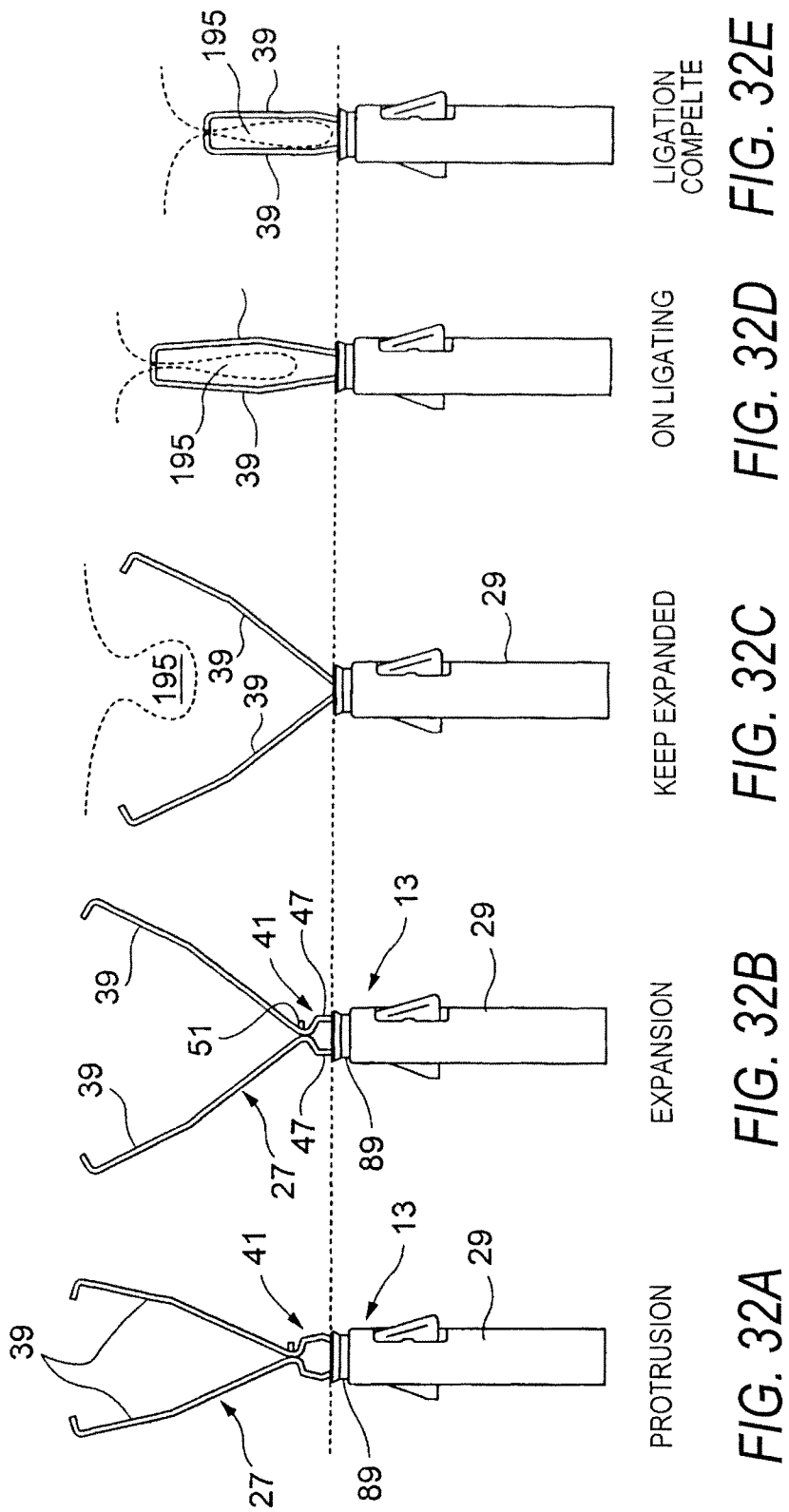

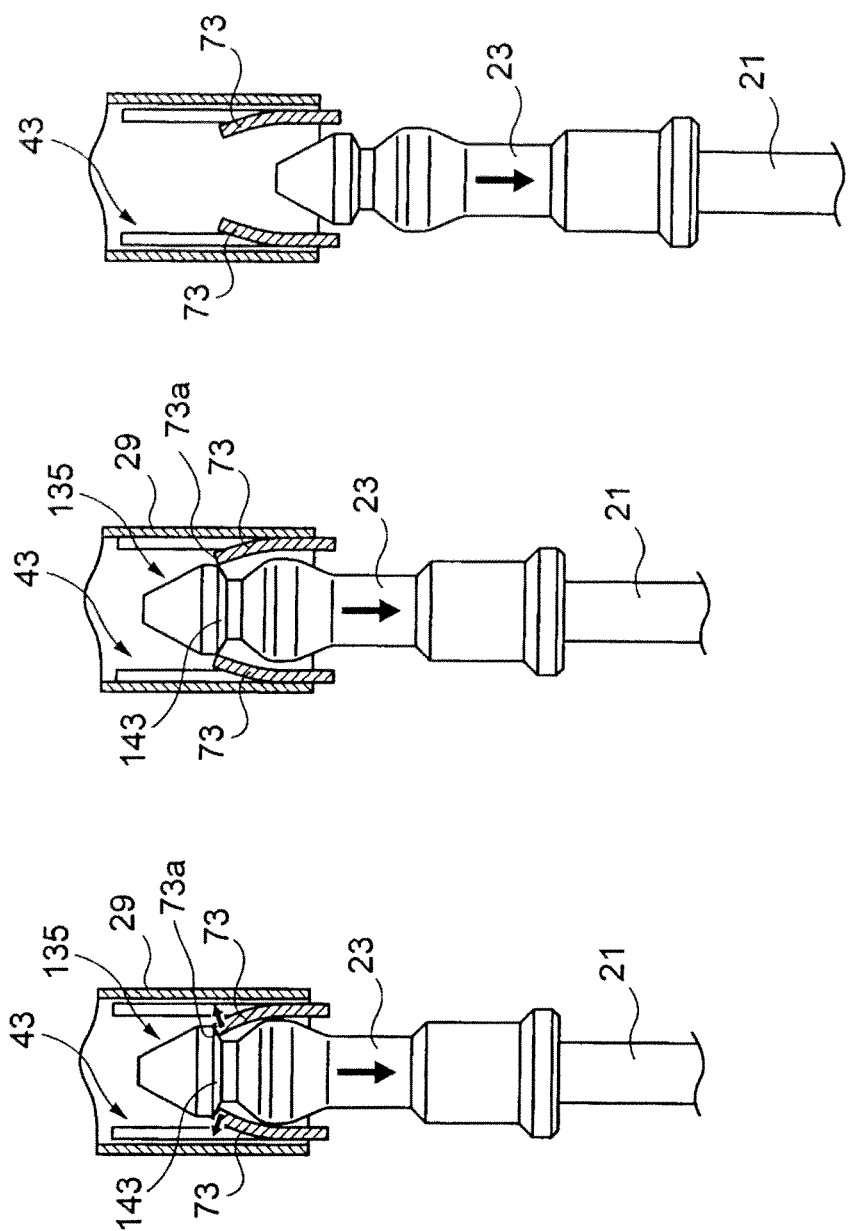

CLIP UNIT AND LIGATION DEVICE USING THE SAME

CROSS-REFERENCE TO RELATED APPLICATIONS

This application is based on and claims priority under 35 USC 119 from Japanese Patent Application No. 2011-202024 filed on Sep. 15, 2011; the entire content of which is incorporated herein by reference.

BACKGROUND OF THE INVENTION

1. Technical Field

The invention relates to a clip unit and a ligation device using the same.

2. Related Art

In general, a ligation device includes a clip unit located at a front end of an elongated flexible sheath extending from a handle manipulation unit. The clip unit is driven by reciprocating a manipulation wire, which is inserted through the sheath, in the axial direction of the sheath or by rotating the manipulation wire around the axis of the sheath at the handle manipulation unit. An endoscope operator may introduce the clip unit into a body cavity by inserting the sheath of the ligation device into a treatment instrument insertion channel formed in an insertion part of the endoscope. This type of ligation device is described, for example in Patent Document 1 (JP-B-4116049) and Patent Document 2 (JP-B-4472719).

A clip unit 301 is embedded in a sheath 303 as illustrated in FIG. 47A when introduced into a body cavity, and the clip unit 301 extends to the outside and revealed from the front end of the sheath 303 as illustrated in FIG. 47B when arriving at a target affected part. The clip unit 301 is provided with flap parts 305, 305 elastically biased diametrically outward, so that when the flap parts 305, 305, which have been closed within the sheath, protrude from the sheath 303, the flap parts 305, 305 are expanded diametrically outward. Once the flap parts 305, 305 are expanded, when the clip unit 301 is pulled into the sheath 303 side, the rear end of the flap parts abuts against the front end of the sheath, thereby being stopped. As a result, the clip unit 301 is positioned in relation to the sheath 303, in which the position is set as a treatment starting position.

SUMMARY OF THE INVENTION

However, both the flap parts 305, 305 of the clip unit 301 illustrated in FIG. 47B are kept expanded diametrically outward by elastic resilience. For that reason, the expansion extent of the flap parts may be fluctuated due to various variations in manufacturing, such as a difference in quality of material and a dimensional error of the flap parts. Due to the fluctuation of the expansion extent of the flap parts, the flap parts may sometimes abut abnormally against the front end of the sheath such that the clip unit 301 is positioned at a slant in relation to the axis of the sheath.

In addition, the positioning posture of the clip unit 301 may be influenced by the variation in the sheath 303 side besides the fluctuation in the flap parts. Since the sheath 303 is repeatedly used after replacing the clip unit 301 as well as suffers from various manufacturing changes like the flap parts, a dimensional change caused by, for example, abrasion may occur in the sheath 303. Like this, it is sometimes impossible to normally set the clip unit 301 to coincide with the axis of the sheath when the clip unit 301 is positioned in relation to the front end of the sheath 303.

Thus, the object of the present invention is to provide a clip unit that can always be precisely positioned in relation to a sheath member to axially coincide with the sheath member, and a ligation device using the same, and to enable a smooth and reliable ligation action.

(1) According to an aspect of the invention, a clip unit for ligating a biological body includes: a clip body having a pair of arm parts; and a fastening ring arranged in an outside of the clip body, and configured to fasten the arm parts, in which: the fastening ring includes a flap part configured to expand diametrically outward from the fastening ring, and a flap retaining unit configured to retaining an expansion extent of the flap part at a given extent.

(2) According to another aspect of the invention, a ligation device includes: the clip unit of (1); a flexible elongated sheath member; a transmission member inserted into the sheath member to be capable of being reciprocated, and configured to transmit driving force to the clip unit connected to the front end of the transmission member; and a manipulation unit arranged on a base end side of the sheath member opposite to the clip unit, and configured to transmit the driving force to the transmission member.

With the inventive clip unit, and the ligation device using the same, the clip unit can always be precisely positioned in relation to a sheath member to axially coincide with the sheath member, and a smooth and reliable ligation action is enabled.

BRIEF DESCRIPTION OF THE DRAWINGS

FIGS. 9A and 9B are a side view of the front end side of the outer fastening ring, and a front view thereof, respectively.

FIGS. 32A to 32E are explanatory views illustrating the actions of the arm parts of the clip unit, from expanding after having protruded to the outside from the front end sheath to ligating a biological tissue, in a step-by-step mariner.

FIGS. 39A to 39C are explanatory views illustrating a process of releasing the J-shaped claw parts from the engagement in a step-by-step manner.

DETAILED DESCRIPTION OF EMBODIMENTS OF THE INVENTION

Now, exemplary embodiments of the present invention will be described with reference to drawings.

Figure 1:
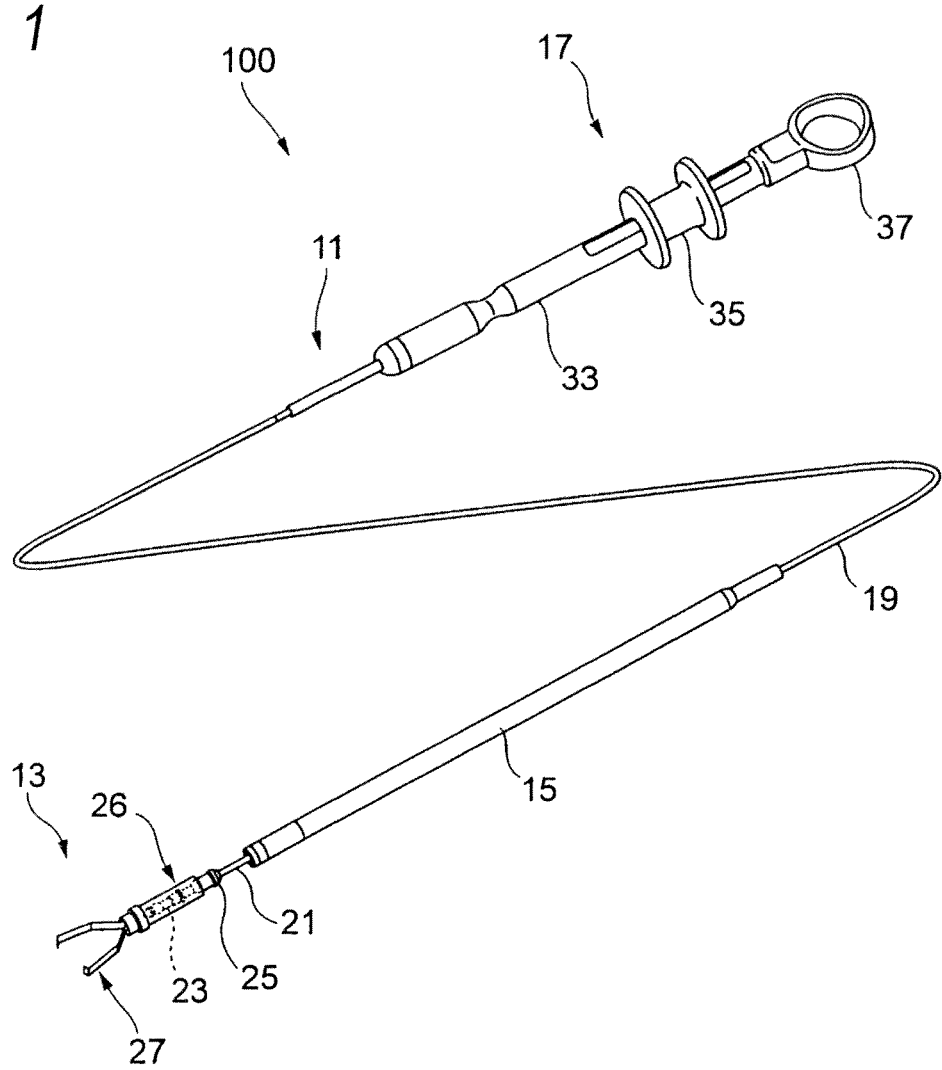
FIG. 1 illustrates an entire configuration of a ligation device for describing an exemplary embodiment of the present invention.

FIG. 1 is an entire configuration view illustrating a ligation device as a medical treatment instrument for describing an exemplary embodiment of the present invention.

A ligation device 100 includes a clip manipulation device 11 which is loaded with a clip unit 13. The clip manipulation device 11 includes a front end sheath 15 configured as an insertion part to be inserted into a channel of an endoscope (not shown) to be inserted into a body cavity, and a handle manipulation unit 17 located at the base end side of the front end sheath 15. The front end sheath 15 and the handle manipulation unit 17 are interconnected by a base end sheath 19, and a manipulation wire 21 is inserted through the inside of the front end sheath 15 and the inside of the base end sheath 19 to be capable of being reciprocated in the axial direction.

The front end sheath 15 and the base end sheath 19 are configured as a guide tube formed by, for example, a densely wound stainless steel coil. The manipulation wire 21 is formed by a stranded metal wire with a proper elasticity, such as, for example, a stainless steel and a NiTi alloy. In addition, to the front end of the manipulation wire 21 which is opposite to the handle manipulation unit 17, a hook 23 and a guide bead 25 are fixed in this order from the front end.

The clip unit 13 includes a fastening ring 26 formed as a cylindrical body, and a clip body 27 supported in the fastening ring 26, and the fastening ring 26 is mounted on the hook 23 provided at the front end of the manipulation wire 21.

The handle manipulation unit 17 includes: a manipulation unit body 33 to which the base end side of the base end sheath 19 is fixed to be rotatable about the axis thereof; a slider 35 connected to be restrained from being rotated in relation to the manipulation wire 21; and a finger pull ring 37 provided at the rear end of the manipulation unit body 33 to be rotatable. The slider 35 is arranged to be restrained from being rotated in relation to the manipulation unit body 33 but to be capable of reciprocating in the axial direction of the sheath.

The handle manipulation unit 17 is capable of reciprocating the clip unit 13 connected to the manipulation wire 21 at the front end of the front end sheath 15 in the axial direction of the sheath by relatively moving the manipulation unit body 33 and the slider 35 in a longitudinal direction. In addition, by rotating the manipulation unit body 33 and the slider 35 around the axis thereof, the clip unit 13 connected to the manipulation wire 21 is allowed to be rotated about the sheath axis.

That is, the clip manipulation device 11 is configured such that, when the slider 35 is moved away from the finger pull ring 37, the manipulation wire 21 is moved in the direction for making the manipulation wire 21 protrude forward from the front end sheath 15, and to the contrary, when the slider 35 is moved toward the finger pull ring 37, the manipulation wire 21 is moved in the direction for making the manipulation wire 21 be pulled into the front end sheath 15. In addition, when the manipulation unit body 33 and the slider 35 are rotated around the axis, the manipulation wire 21 is rotated together with the slider 35. The clip unit 13 loaded in the front end side of the manipulation wire 21 is maintained in the state in which it is restrained from being rotated by the hook 23, which will be described later. Accordingly, the clip unit 13 is released by the extension of the manipulation wire 21, and rotationally driven by the rotation of the manipulation wire 21.

The manipulation wire 21 is capable of using an appropriate wire which may readily transmit the rotation of one end thereof to the other end. For example, even a torque wire may be used which is difficult to produce rollover. In addition, a cable obtained by wire-drawing a stainless steel may be also used.

In the following description, a direction directed toward the finger pull ring 37 of the handle manipulation unit 17 of the ligation device 100 is referred to as a base end direction or rear side, and a direction directed toward the front end of the clip body 27 is referred to as a distal end direction or front side. In addition, the axial direction of the fastening ring 26 of the clip unit 13, as well as the axial direction of the front end sheath 15, the base end sheath 19, and the manipulation wire 21 will be referred to as a longitudinal axis direction.

<Clip Unit>

Next, the configuration of the clip unit 13 will be described in detail.

Figure 2:
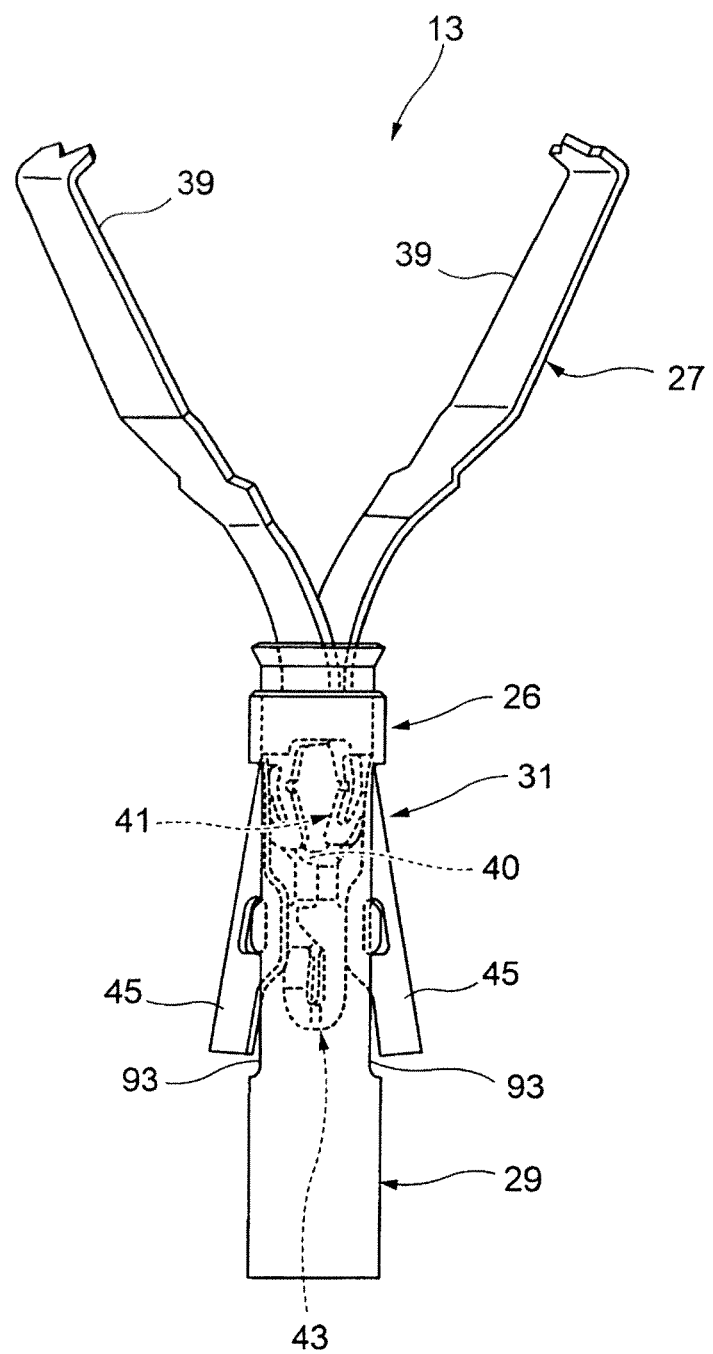
FIG. 2 is illustrates the configuration of a clip unit partially in cut-away.
Figure 3:
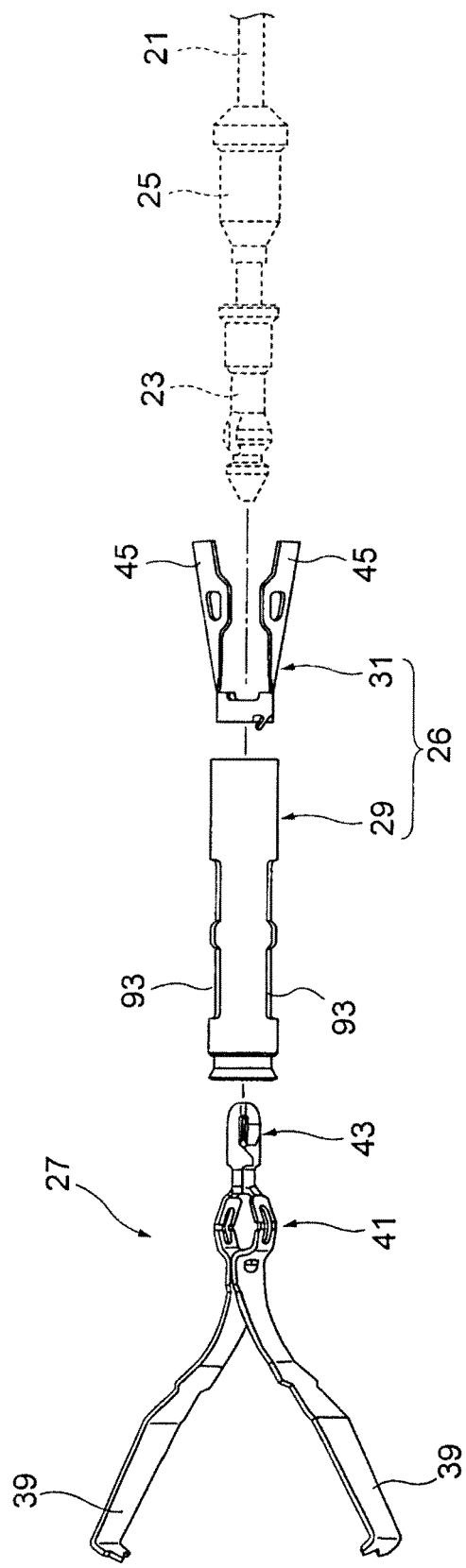
FIG. 3 is an exploded perspective view of the clip unit illustrated in FIG.

FIG. 2 is a configuration view illustrating, partially in cut-way, the clip unit, and FIG. 3 is an exploded perspective view of the clip unit. The clip unit 13 includes a fastening ring 26 and a clip body 27. The fastening ring 26 is constituted with an outer fastening ring 29 formed as a cylindrical body, and an inner fastening ring 31 inserted into the inside of the cylindrical body of the outer fastening ring 29.

The clip body 27 includes: a pair of arm parts 39, 39 which are expanded and biased in relation to each other; abuse end section 41 formed in a loop shape for interconnecting the base ends of the arm parts 39, 39; a connection tail section 43 formed on the base end section 41 at the side opposite to the pair of arm parts 39, 39 (at the rear side). The arm parts 39, 39 may be closed to each other when inserted into the fastening ring 26, so that a biological tissue can be grasped by the arm parts 39, 39.

All the clip body 27, the outer fastening ring 29, and the inner fastening ring 31 may be formed from a metallic material, such as a stainless steel. The clip body 27 is formed by bending a band-shaped resilient metallic plate material in a U-shape. The outer fastening ring 29 is a cylindrical member and accommodates the inner fastening ring 31 within the inside thereof. The inner fastening ring 31 includes a pair of flap parts 45, 45 which are configured to be expanded and biased diametrically outward by elastic resilience.

The outer fastening ring 29 is formed with a pair of flap protruding holes 93, 93 at positions corresponding to the flap parts 45, 45 of the inner fastening ring 31, so that when the inner fastening ring 31 is accommodated in the outer fastening ring 29, the flap parts 45, 45 partially protrude radially outward from the flap protruding holes 93, 93.

The clip unit 13 is formed by inserting the base end section 41 and the connection tail section 43 of the clip body 27 into the outer fastening ring 29, which accommodates the inner fastening ring 31, from the front side of the outer fastening ring 29. A hook 23 is engaged with the clip unit 13, in which the hook 23 is provided at the front end of the manipulation wire 21 and inserted into the clip unit 13 from the rear side of the clip unit 13.

<Clip Body>

Figure 4:
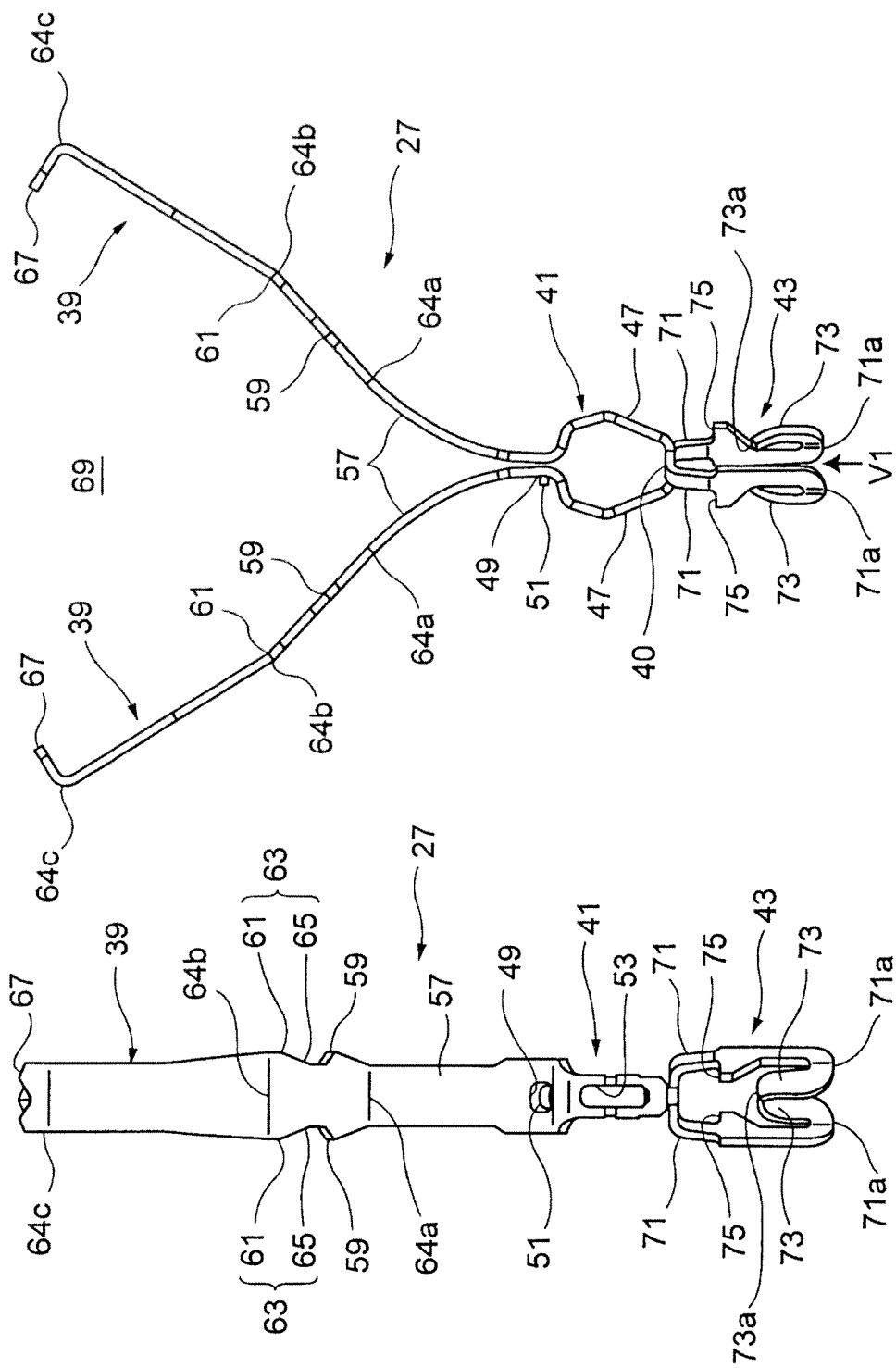
FIGS. 4A and 4B are a side view and a front view of the clip body, respectively.
Figure 5:
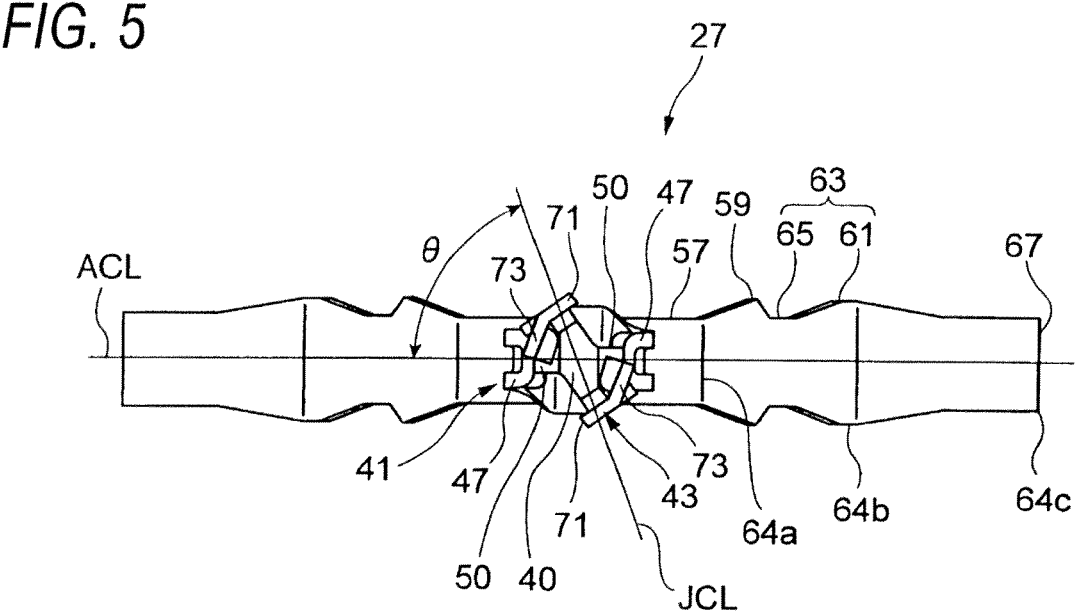
FIG. 5 is a bottom view of the clip body shown in the direction indicated by arrow V1 in FIG. 4B.

FIGS. 4A and 4B are a side view and a front view of the clip body, respectively, and FIG. 5 is a bottom view of the clip body viewed in the direction indicated by arrow V1 in FIG. 4B.

The clip body 27 is formed by bending a band-shaped metallic plate material in such a mariner that a pair of the arm parts 39, 39, the base end section 41 and the connection tail section 43 are integrally formed. The base end section 41 and the connection tail section 43 extend from the connection base section 40 which has a flat surface which is perpendicular to the longitudinal central axis of the clip body 27. A pair of loop parts 47, 47 extend from the connection base section 40 and abut against each other at the arm part 39 side of the loop parts 47, 47 (loop ends), whereby the base end section 41 is formed in a loop shape in the entirety. The loop parts 47, 47 are arranged symmetrically, and connected to the arm parts 39, 39, respectively, in the side opposite to the connection base section 40.

At the abutting loop ends, one of the loop parts 47, 47 is formed with an engagement hole 49, and the other of the loop parts 47, 47 is formed with a deviation prevention claw 51 for engaging with the engagement hole 49. As the engagement hole 49 and the deviation prevention claw 51 are engaged with each other, the pair of arm parts 39, 39 are prevented from being deviated in the longitudinal axis direction and in the direction perpendicular to the longitudinal axis direction. In addition, each of the loop parts 47, 47 is formed with a slit part 53 along the loop.

The arm parts 39, 39, which are provided to extend further beyond the loop end of the loop parts 47, 47, are formed by band-shaped resilient metallic plate material members which are symmetrically arranged to be opposed to each other. The arm parts 39, 39 include: linear plate parts 57 with a predetermined width in the direction perpendicular to the expanding direction of the arm parts 39, 39; disengagement prevention protrusions 59 which are wider than the linear plate parts 57; middle parts 63, each of which is formed with a pull-in prevention protrusion 61 via a taper part 65; and front end parts 67 configured to be capable of grasping a biological tissue therebetween, in this order from the base end section 41. The arm parts 39, 39 are biased to be expanded from each other with reference to the engagement hole 49 and the deviation prevention claw 51 by the elastic resilience of the clip body 27.

A pair of the arm parts 39, 39 are formed in circular arc shapes with a curvature in such a manner that the linear plate parts 57 are bulging inwardly each other. At the front end sides of the linear plate parts 57, first bending points 64a are provided where the arm parts 39, 39 are bent outward, and in the vicinity of the pull-in prevention protrusions 61 of the middle parts 63, second bending points 64b are provided where the arm parts 39, 39 are bent inwardly. In addition, the arm parts 39, 39 are inwardly bent at third bending points 64c positioned closer to the front end side than the middle parts 63, thereby forming the front end parts 67.

When a pair of the arm parts 39 are opened by the elastic resilience of the clip body 27, the pair of front end parts 67, 67 are largely spaced from each other, thereby forming a grasping gap 69 between the front end parts 67, 67. When the arm parts 39 are closed, the front end parts 67, 67 approach each other to be capable of grasping a biological tissue. In addition, as illustrated in FIG. 4, each of the front ends of the front end parts 67, 67 may be formed to have an obtuse-angled convex part and an obtuse-angled concave part to be engaged with each other, or may have a linear shape.

The connection tail section 43 includes: a pair of plate-shaped arms 71 extending from the connection base section 40 of the base end section 41 in the direction opposite to the pair of arm parts 39; and J-shaped claw parts 73 as engagement claw parts, which are U-turned at the rear ends 71a of the arms 71, respectively, and extend from the rear ends 71a of the arms 71 toward the front side (in the direction to the arm parts 39). The pair of arms 71 define a space for accommodating the hook 23. Each of the J-shaped claw parts 73 is inclined inwardly at the front end 73a in advance, in which the J-shaped claw parts 73 are inclined more inwardly than the arms 71. In addition, each of the arms 71 extending from the connection base section 40 with a predetermined width has a wider part at the central area thereof, and engagement step parts 75 are formed by the wider parts.

As illustrated in FIG. 5, the connection tail section 43 is formed in such a manner that an arm part center line ACL and a connection tail section center line JCL are different in phase by an angle θ (for example, 40 degrees to 70 degrees, preferably 55 degrees to 60 degrees), wherein the arm part center line ACL extends through the center of the pair of arm parts 39 which are provided to extend from the base end section 41, and the connection tail section center line JCL extends through the center of a pair of arms 71 of the connection tail section 43 which are provided to extend from the connection base section 40 of the base end section 41. That is, the expansion direction of the arm parts 39 are determined to intersect the expansion direction of the connection tail section 43 with the angle θ.

In addition, the loop parts 47, 47 of the base end section 41 are connected to the side surfaces of the flat part of the connection base section 40 via constricted spots 50 illustrated in FIG. 5 (see FIG. 8B), respectively. As a pair of the loop parts 47, 47 are connected to the connection base section 40 via the constricted spots 50, external forces applied to the arm parts 39, 39 are retrieved at the constricted spots 50, and deformation is prevented from reaching the connection base section 40 and the connection tail section 43. The constricted spots 50 also prevent external forces from reaching the arm parts 39, 39 from the connection tail section 43.

<Inner Fastening Ring>

Figure 6:
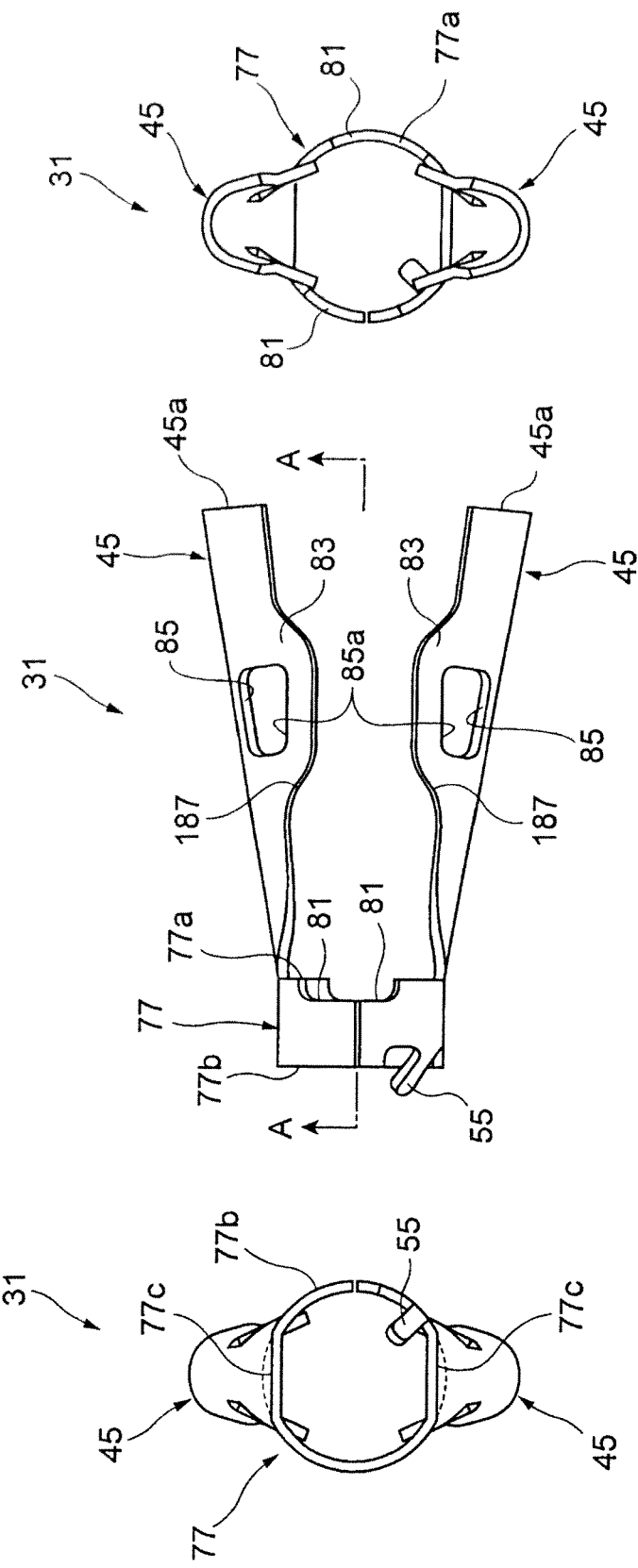
FIGS. 6A and 6B are a side view and a front view of the front end side of an inner fastening ring, respectively.
FIG. 6C is the side view of the rear end side of the inner fastening ring.
Figure 7:
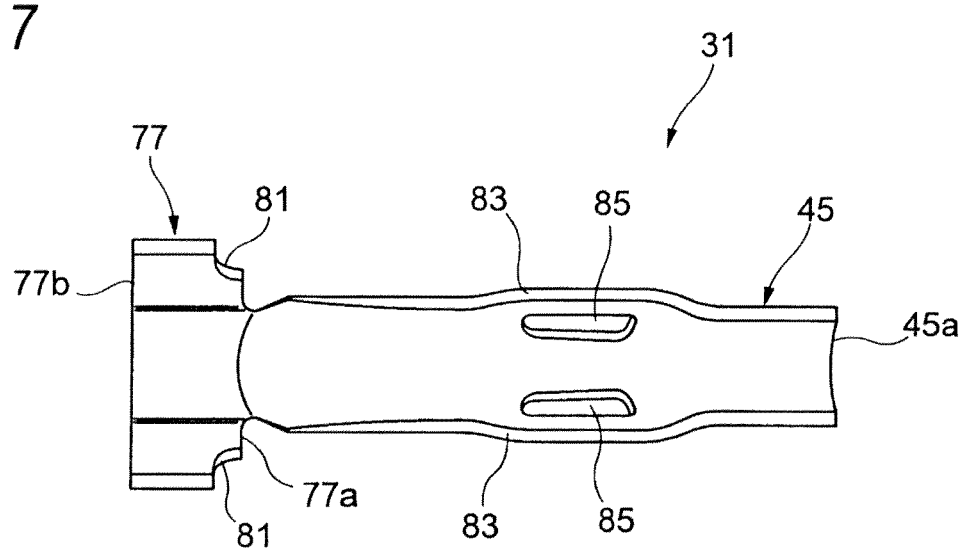
FIG. 7 is a cross-sectional view taken along line A-A in FIG. 6B.

FIGS. 6A and 6B are a side view and a front view of the front end side of the inner fastening ring, respectively, and FIG. 6C is a side view of the rear end side of the inner fastening ring. FIG. 7 illustrates a cross-sectional view taken along line A-A in FIG. 6B.

The inner fastening ring 31 includes a ring part 77, and a pair of flap parts 45, 45 cantilevered on the ring part 77, more specifically extending from a one side end face 77a. The pair of flap parts 45, 45 are formed by slightly expanding free ends 45a from the axial direction at two diametrically outer edge positions on the one side end face 77a of the ring part 77.

On the one side end face 77a to which the flap parts 45, 45 are connected, a pair of recesses 81, 81 are formed, and the engagement step parts 75 of the clip body 27 (see FIG. 4) are engaged in the recesses 8), 81, respectively. In addition, on the front end face 77b of the ring part 77 opposite to the one side end face 77a, an expansion retaining protrusion 55 is formed to protrude from the ring part 77 to an inclined front side facing diametrically inward. The expansion retaining protrusion 55 will be described later.

Each of the flap parts 45, 45 is formed to have a circular arc shape in a diametrical cross-section perpendicular to the axial direction, and is formed with a bulge part 83 opposite to the other flap part 45 at the axially central area thereof, in which the length of the circular arc in the diametrical cross-section is increased at the bulge part 83. The bulge parts 83 are formed with flap locking holes 85, 85, respectively. The inner fastening ring 31 is formed in such a manner that when the flap parts 45 are closed, the outer diameter of the inner fastening ring 31 is substantially equal to or slightly smaller than the inner diameter of the outer fastening ring 29.

Figure 8A:
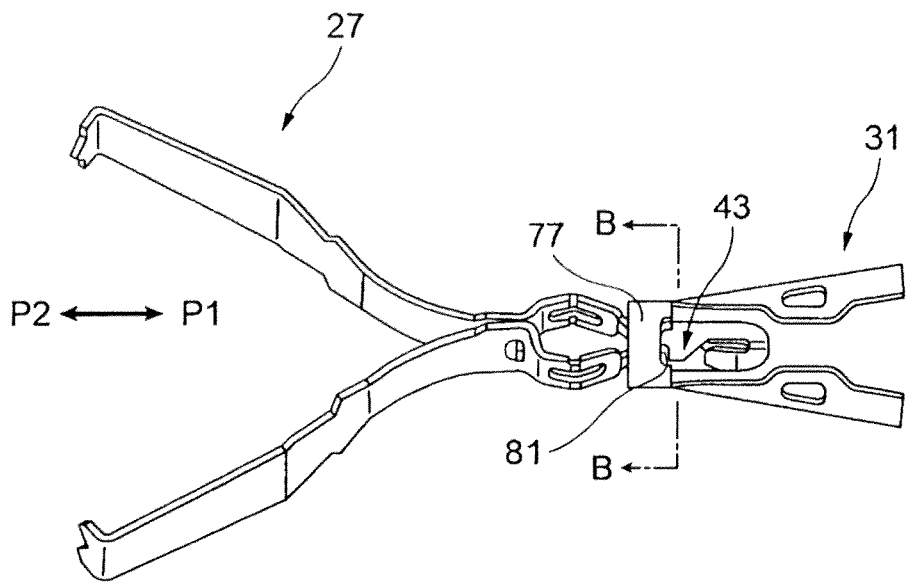
FIG. 8A is a perspective view illustrating a state in which the clip body and the inner fastening ring are engaged with each other without showing an outer fastening ring.
Figure 8B:
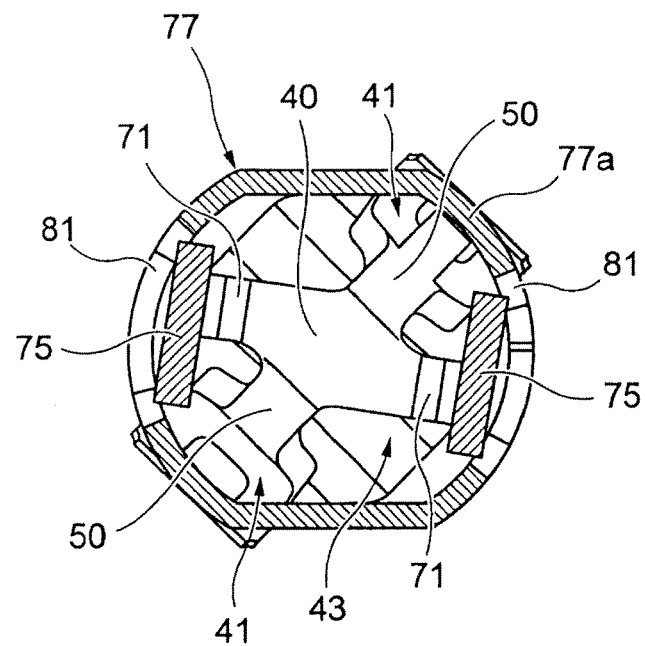
FIG. 8B is a cross-sectional view taken along line B-B in FIG. 8A.

The inner fastening ring 31 and the clip body 27 are engaged with each other as follows. FIG. 8A is a state in which the clip body 27 and the inner fastening ring 31 are engaged with each other without showing an outer fastening ring 29, and FIG. 8B is a cross-sectional view taken along line B-B in FIG. 8A. As shown in FIG. 8A, the connection tail section 43 of the clip body 27 is inserted into the ring part 77 of the inner fastening ring 31 in the P1 direction in FIG. 8A. At this time, as illustrated in FIG. 5B, the engagement step parts 75 of the connection tail section 43 are snugly fitted in the recesses 81 provided in the one side end face 77a of the ring part 77, such that the engagement step parts 75 and the recesses 81 are engaged with each other. Accordingly, even when an attempt is made to pull out the clip body 27 from the inner fastening ring 31 in the P2 direction in FIG. 8A, the engagement step parts 75 and the recesses 81 abut against each other such that they cannot be separated from each other.

<Outer Fastening Ring>

Figure 10:
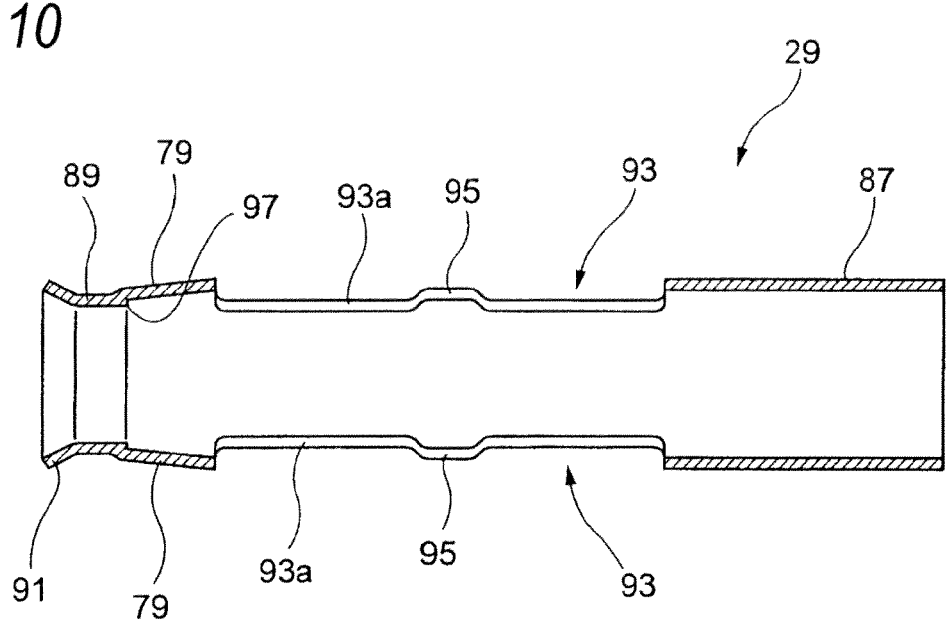
FIG. 10 is a cross-sectional view taken along line C-C in FIG. 9A.

FIGS. 9A and 9B are a side view at the front end side and a front view of the outer fastening ring, respectively, and FIG. 10 is a cross-sectional view taken along line C-C in FIG. 9A.

The outer fastening ring 29 includes a cylindrical section 87, a constricted spot 89 formed by reducing the diameter of the cylindrical section 87 in the vicinity of the front end of the cylindrical section 87, and a taper section 91 extending from the constricted spot 89 in such a manner that the diameter of the taper section 91 is gradually increased as approaching the front end side. The inner diameter of the cylindrical section 87 is slightly larger than the outer diameter of the ring part 77 of the inner fastening ring 31 (see FIG. 6), such that the inner fastening ring 31 is capable of being fitted in the inside of the outer fastening ring 29. In addition, in the cylindrical section 87, a pair of flap protruding holes 93 are formed to be elongated along the axis, wherein the flap protruding holes 93 are arranged opposite to each other. Each longer side 39a forming the periphery of each of the flap protruding holes 93 is formed with flap opening prevention taps 95, 95 substantially at the central areas thereof in such a manner that the flap opening prevention taps 95, 95 protrude toward one another in the circumferential direction of the cylindrical section 87.

As illustrated in FIG. 9A, the inner face of the constricted spot 89 of the outer fastening ring 29 is formed in a substantially oval shape, so that the diameter of the major axis DL and the diameter of minor axis DS are formed in different sizes. Line C-C in FIG. 9A is a line that interconnects the centers of the widths of the flap protruding holes 93, 93 in the circumferential direction, wherein line C-C indicates a central position in the circumferential direction where the flap protruding holes 93, 93 are formed. The line C-C has a slope of a predetermined angle (for example, about 45°), and the flap protruding holes 93, 93 are formed to correspond the phase angle of the connection tail section 43 of the clip body 27.

As illustrated in FIG. 10, an inner diameter step part 97 is formed over the entire circumference of the boundary of the inner peripheries of the cylindrical section 87 and the constricted spot 89. Between the cylindrical section 87 and the constricted spot 89, a pair of planar parts 79 are formed at circumferential positions substantially the same with the flap protruding holes 93, wherein the planar parts 79 gradually reduce the diameter from the outer diameter of the cylindrical section 87 to an outer diameter in the vicinity of the outer diameter of the constricted spot 89 along the axis.

For this reason, the diametrical cross-sectional shape of the area of the planar part 79 between the cylindrical section 87 and the constricted spot 89 has parallel parts formed by the planar parts 79 and circular arc parts formed by the cylindrical section 87. This diametrical cross-sectional shape is similar to the diametrical cross-sectional shape of the ring part 77 (see FIG. 6) of the inner fastening ring 31, and the inner diameter of the outer fastening ring 29 is slightly larger than the outer diameter of the ring part 77 of the inner fastening ring 31.

Figure 11:
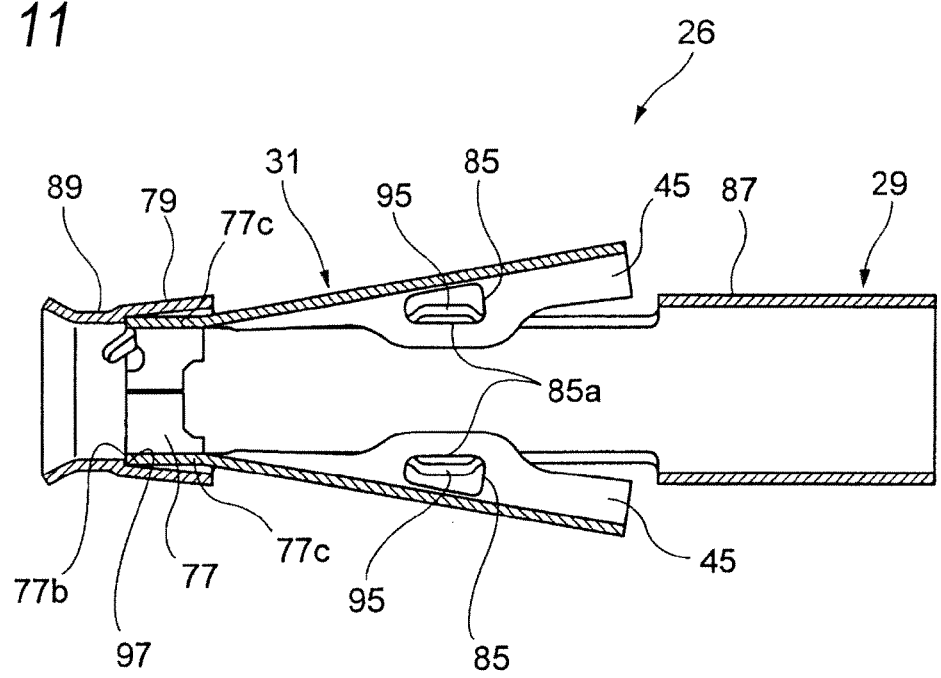
FIG. 11 is a cross-sectional view illustrating the outer fastening ring and the inner fastening ring in the state where they are engaged with each other.

FIG. 11 is a cross-sectional view illustrating the outer fastening ring 29 and the inner fastening ring 31 in a state where they are engaged with each other.

The outer fastening ring 29 and the inner fastening ring 31 are engaged with each other by inserting the inner fastening ring 31 into the cylindrical section 87 of the outer fastening ring 29 in such a manner that the ring part 77 side is positioned at the forefront. The inner fastening ring 31 is positioned in the axial direction as the front end face 77b of the ring part 77 abuts against the inner diameter step part 97 of the constricted spot 89. In addition, the position of the inner fastening ring 31 in the rotating direction is determined by fitting the planar parts 77c of the ring part 77 of the inner fastening ring 31 in the inner periphery of the parts formed with the planar parts 79 in the outer fastening ring 29, and fitting the ring part 77 of the inner fastening ring 31 in the outer fastening ring 29.

In addition, the flap opening prevention taps 95 of the outer fastening ring 29 are respectively inserted into the flap locking holes 85 provided in the pair of flap parts 45 of the inner fastening ring 31, and the flap opening prevention taps 95 respectively abut against one side 85a of the flap locking holes 85. As a result, the flap parts 45 configured to be expanded by elastic resilience are prevented from being excessively opened by abutting against the flap opening prevention taps 95, and the expansion angle of the flap parts 45 can be securely maintained at a predetermined angle established at the time of design.

In addition, since the maximum outer diameter of the loop parts 47 of the clip body 27 is determined in a size that makes the loop parts 47 abut against the taper section 91 of the outer fastening ring 29, the inner fastening ring 31 and the clip body 27, which are formed integrally with each other, are prevented from being deviated to the rear side in relation to the outer fastening ring 29. Furthermore, the clip body 27 is inseparably engaged with the inner fastening ring 31. For this reason, the clip body 27 and the outer fastening ring 29 will not be deviated from each other by vibration at the time of transportation or the like.

<Handle Manipulation Unit>

Figure 12:
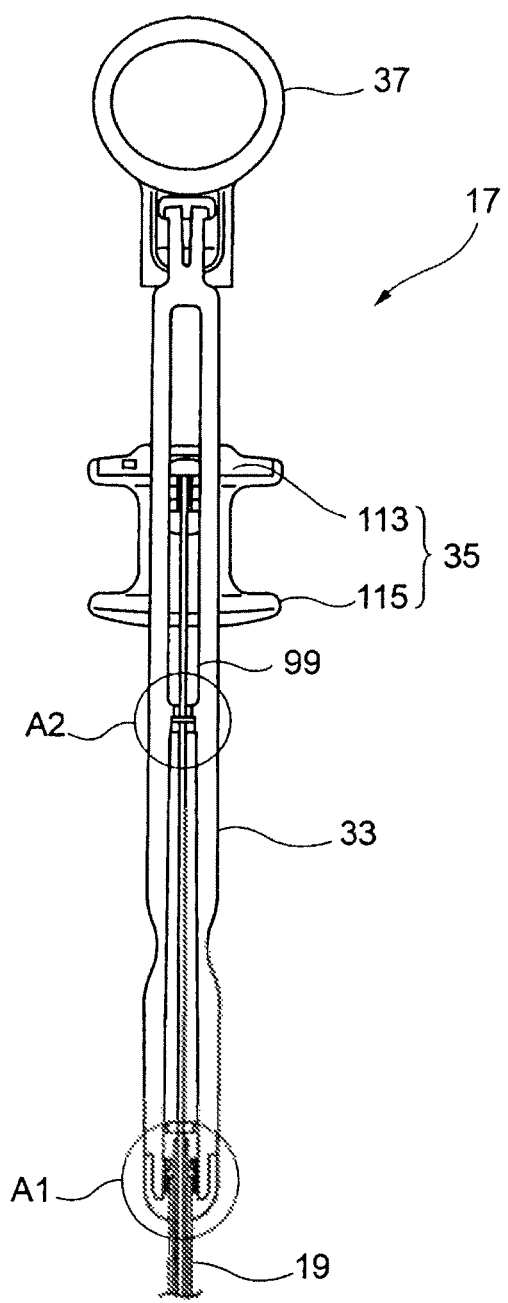
FIG. 12 is a cross-sectional view of the handle manipulation unit of the ligation device.

FIG. 12 is a cross-sectional view of the handle manipulation unit of the ligation device.

As described above, the handle manipulation unit 17 includes a manipulation unit body 33 to which the base end side of the base end sheath 19 is fixed to be rotatable around the axis, a slider 35, and a finger pull ring 37. The manipulation unit body 33 is provided with a slitting section 99 formed with a slit along the axial direction, and the slider 35 is configured to be movable in the axial direction within the slit forming extension. The slider 35 consists of a slider body 115 and a manipulation wire anchor 113.

Figure 13:
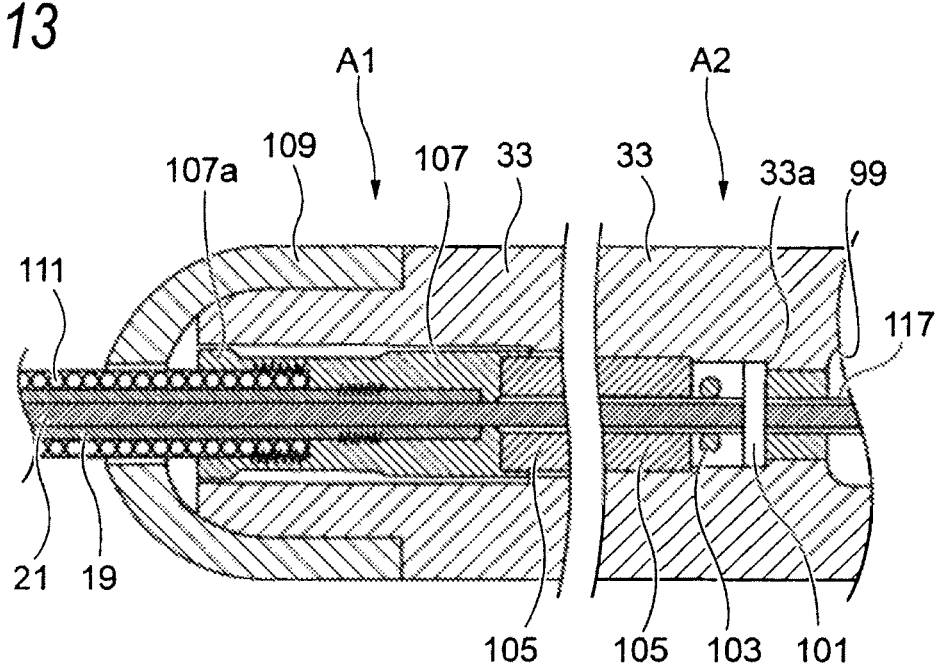
FIG. 13 is an enlarged cross-sectional view of the front end part of the manipulation unit body and an area in the vicinity of the front end part of the slitting section illustrated in FIG. 12.

FIG. 13 is an enlarged cross-sectional view of the front end part A1 of the manipulation unit body 33 and a part A2 in the vicinity of the front end part of the slitting section 99 illustrated in FIG. 12.

A fixing clasp 107 is provided at the front end of the manipulation unit body 33, wherein a base end sheath 19 with the manipulation wire 21 inserted therein, and an bending prevention spring 111 configured to cover and protect the base end sheath 19 are inserted into the front end part 107a of the fixing clasp 107 along the axis. On the front end of the manipulation unit body 33, a cap 109 is press-fitted.

The manipulation wire 21, which extends out from the base end sheath 19, extends to the slider 35 from the base end of the fixing clasp 107. The manipulation wire 21 is inserted which is covered by the buckling prevention pipe 117 through the guide pipe 105 arranged in the base end side of the fixing clasp 107. The guide pipe 105 extends to an area in the vicinity of the front end part of the slitting section 99 to slidably accommodate the buckling prevention pipe 117. In addition, the buckling prevention pipe 117 extends to the slider 35 to retain the manipulation wire 21 in the linear shape.

The front end of the buckling prevention pipe 117 is slidably fitted in the guide pipe 105, and when the slider 35 is slid, specifically, when the slider 35 is moved in the direction opposite to the finger pull ring 37, the buckling prevention pipe 117 prevents the occurrence of buckling of the manipulation wire 21, thereby enabling the stable manipulation of the manipulation wire 21.

In the base end side of the guide pipe 105, there are provided an O-ring 103 and a washer 101. The washer 101 is locked by a stepped part 33a of the manipulation unit body 33 to restrain the axial movement of the O-ring 103. The inner diameter of the washer 101 is smaller than the outer diameter of the O-ring 103 to prevent the O-ring 103 from escaping to the rear side. In addition, a gap is provided between the washer 101 and the guide pipe 105, and a gap is also provided between the O-ring 103 and the guide pipe 105.

The buckling prevention pipe 117 is inserted through the guide pipe 105, the O-ring 103 and the washer 101 with a proper gap for enabling the rotation of the buckling prevention pipe 117. The inner diameter of the guide pipe 105 is determined as a size that enables the insertion of the buckling prevention pipe 117, and provides a little clearance for the manipulation wire 21. The guide pipe 105 and the fixing clasp 107 are configured to be rotatable in relation to each other. The inner diameter of the O-ring 103 and the outer diameter of the buckling prevention pipe 117 have a relationship in size such that they are rotatable around the axis, and frictional resistance is produced in the axial direction. The parts depicted by dotted lines in FIG. 13 indicate welded parts.

Figure 14:
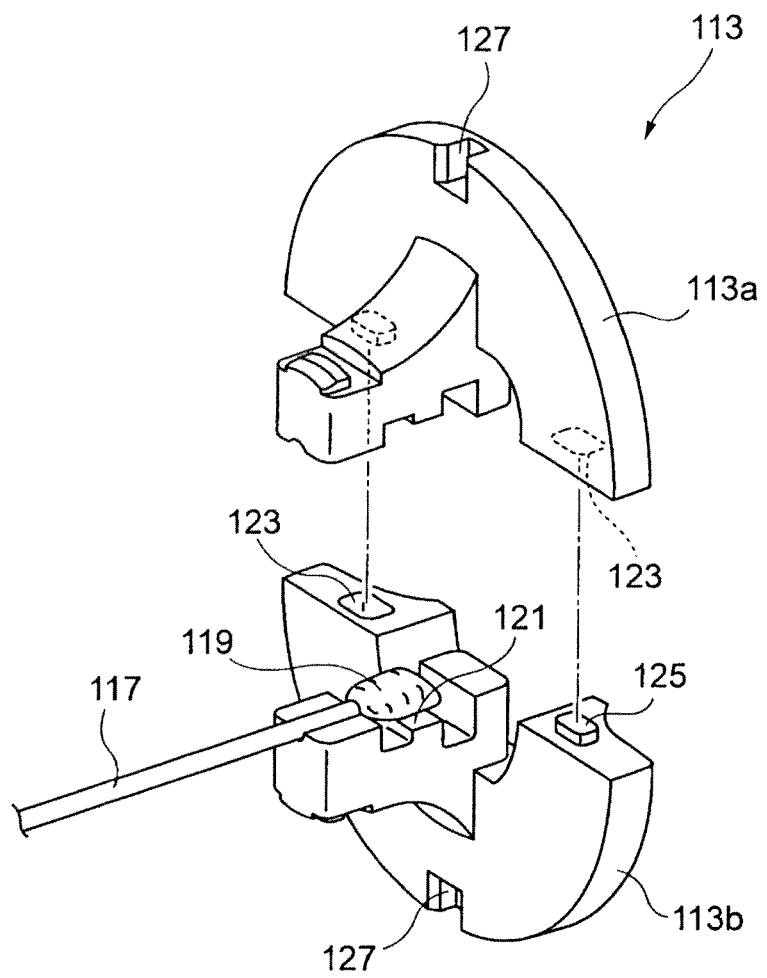
FIG. 14 is an exploded perspective view of a manipulation wire anchor for anchoring the manipulation wire to a slider.
Figure 15:
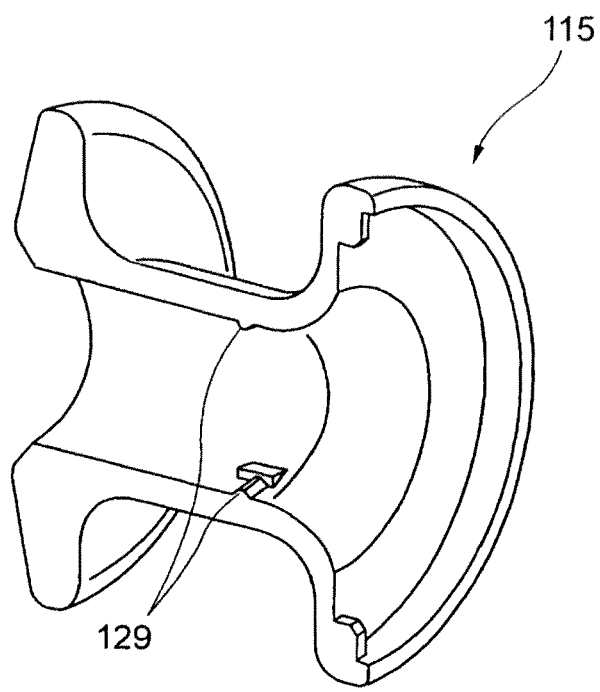
FIG. 15 is a sectioned perspective view of the slider body.

FIG. 14 is an exploded perspective view of a manipulation wire anchor for anchoring the manipulation wire 21 to the slider 35, and FIG. 15 is a sectioned perspective view of the slider body.

The slider 35 is comprised of a slider body 115 and a manipulation wire anchor 113 configured in a halved structure. The slider 35 is fabricated by combining the manipulation wire anchor 113 with the slider body 115 fitted in the manipulation unit body 33 across the slitting section 99 (see FIG. 12) and press-fitting and fixing the manipulation wire anchor 113 to the slider body 115. The slider body 115 and the manipulation wire anchor 113 combined thereby become slidable along the slitting section 99.

As illustrated in FIG. 14, the manipulation wire anchor 113 consists of a top wire anchor 113a and a bottom wire anchor 113b, each of which is substantially semi-circular. The top wire anchor 113a and the bottom wire anchor 113b have the same shape obtained by halving the manipulation wire anchor 113. Both the anchors 113a and 113b have a recess 121 for accommodating a caulking clasp 119 (illustrated in the drawing as a flat shape after mashed) fixedly attached to the rear end of the buckling prevention pipe 117. The top wire anchor 113a and the bottom wire anchor 113b are combined with each other with depressions 123 and protrusions 125. In addition, the bottom wire anchor 113b has a pair of recesses 127, 127 which are engaged with a pair of latching claws 129, 129 of the slider body 115 illustrated in FIG. 15 to prevent relative rotation thereof as well as to conduct positional alignment thereof.

The buckling prevention pipe, the wire and the caulking clasp are integrated with each other by fitting the buckling prevention pipe 117 over the wire, fitting the caulking clasp 119 over the buckling prevention pipe 117, and then caulking the caulking clasp with a pressing tool or the like. The caulking clasp 119 is turned to a non-circular shape through the caulking process, and its relative rotation in relation to the manipulation wire anchor 113 is blocked. As a result, the buckling prevention pipe 117 is fixed to the manipulation wire anchor 113 together with the manipulation wire 21 inserted through the buckling prevention pipe 117.

When performing manipulation by the handle manipulation unit 17 configured as described above, a thumb is inserted into the finger pull ring 37, and the index finger and the middle finger of the same hand are positioned to grasp the slider 35 therebetween. In addition, in order to rotate the clip unit around the axis, the manipulation unit body 33 is rotated.

The rotation of the manipulation unit body 33 is transmitted to the slider 35 and the manipulation wire 21 from the manipulation unit body 33, as illustrated in FIG. 13. In addition, since the manipulation unit body 33 and the fixing clasp 107 are rotatably fixed, the rotation of the manipulation unit body 33 is not transmitted to the sheaths 19, 15 including the fixing clasp 107. That is, by rotating the manipulation unit body 33, the manipulation wire 21 is rotated but the base end sheath 19 and the front end sheath 15 are not rotated.

<Front End Sheath>

Figure 16:
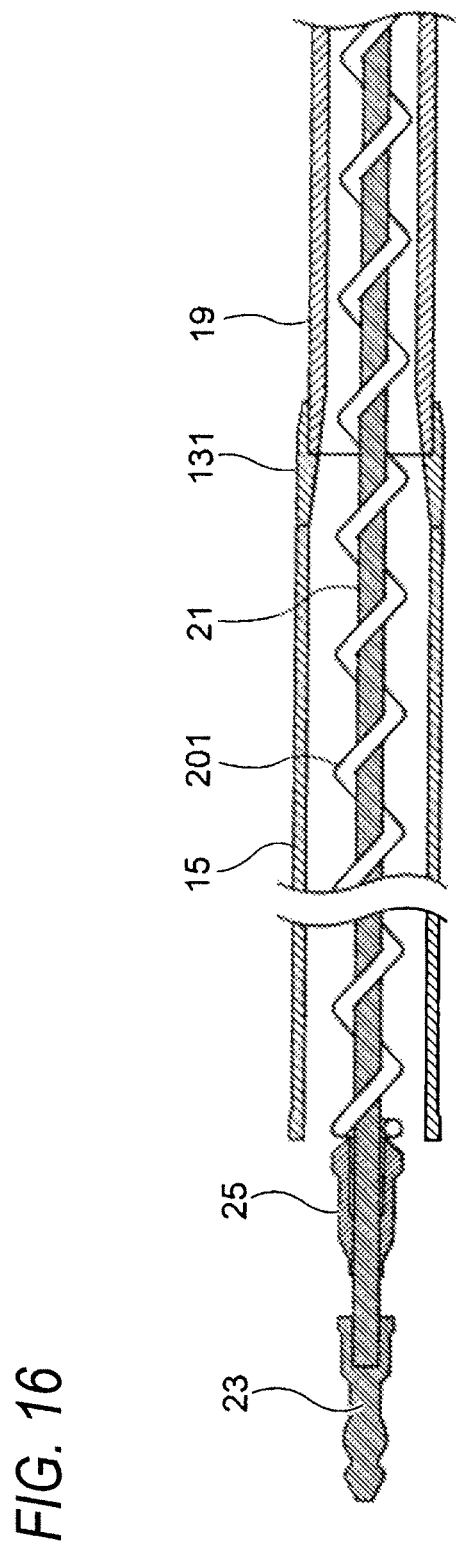
FIG. 16 is a cross-sectional view of a front end sheath.

FIG. 16 is a cross-sectional view of the front end sheath. At the base end of the front end sheath 15, the front end part of the base end sheath 19 is welded via a connection ring 131. The inner diameter of the front end sheath 15 is slightly larger than the outer diameter of the outer fastening ring 29 (see FIG. 9), so that the outer fastening ring 29 can be accommodated in the front end sheath 15. The manipulation wire 21 extending from the base end sheath 19 is inserted through the front end sheath 15, and protrudes to the outside toward the front side from the front end sheath 15. At the front end part which is the distal end of the manipulation wire 21, a hook 23 and a guide bead 25 are fixed through soldering or laser welding. As a result, when the slider 35 (see FIG. 2) is slid in the axial direction in relation to the manipulation unit body 33, reciprocating actions are performed following the slide action so as to push the manipulation wire 21 out of the front end sheath 15 to the front side and to return the manipulation wire 21 to the front end sheath 15.

In addition, in the inside of the front end sheath 15 or the base end sheath 19, a retainer coil (a retainer member) 201 is arranged between the front end sheath 15 or the base end sheath 19 and the manipulation wire 21. The retainer coil is formed of a highly wear-resistant hard metal, such as a stainless steel, and is formed in a circular cross-section. By interposing the retainer coil 201 between the inner periphery of the front end sheath 15 or the base end sheath 19 and the manipulation wire 21, the front end sheath 15 or the base end sheath 19 and the manipulation wire 21 do not directly contact with each other and contact with the retainer coil 201 with a small contact area.

For this reason, resistance against the reciprocation of the manipulation wire 21 in the front end sheath 15 or the base end sheath 19 and resistance against the rotation of the manipulation wire 21 may be reduced, and the manipulation wire 21 may be manipulated more smoothly with excellent responsiveness. By determining the hardness of the retainer coil 201 to be substantially equal to that of the manipulation wire 21, the abrasion caused by the sliding movement between the retainer coil 201 and the manipulation wire 21 may be suppressed.

The front end part of the retainer coil 201 is fixedly attached to the guide bead 25, and the retainer coil 201 extends to the handle manipulation unit side. As the retainer coil 201 is arranged in the front end side of the front end sheath where the clip unit is mounted, it is possible to reduce contact resistance in relation to the front end part of the front end sheath which has a lot of opportunities to be curved. For this reason, even if the front end sheath 15 is complicatedly curved, the reciprocation in the axial direction and rotation of the manipulation wire 21 can be smoothly performed. In addition, by fixedly attaching the retainer coil 201 to the guide bead 25, the arranging place of the retainer coil 201 will not be deviated from the front end of the manipulation wire 21.

In addition, the rear end part of the retainer coil 201 is formed as a free end that is not fixed to the front end sheath 15 and the manipulation wire 21. Due to this, the retainer coil 201 becomes extensible within the front end sheath 15, and the rotation of the free end is not restrained. Accordingly, a following performance, such as a curving behavior, can be enhanced.

It is more desirable for the retainer coil 201 to be in a loosely wound condition in which adjacent coil parts are spaced from each other rather than in a closely wound condition in which adjacent coils contact with each other. By forming the retainer coil 201 in the loosely wounded condition, it is possible to further reduce the contact area, thereby further reducing contact resistance. In addition, when cleaning the inside of a sheath, the circulation of cleaning liquid may be facilitated, and the cleaning performance may be improved.

The winding direction of the retainer coil 201 is preferably in a reverse direction to the winding direction for the densely wound coils of the front end sheath 15 and the base end sheath 19. In addition, the winding direction of the retainer coil 201 is preferably in a reverse direction to the winding direction of the stranded wire of the manipulation wire 21. In such a case, it is possible to prevent the retainer coil 201 from penetrating into gaps between strands in the inner surface of a sheath member or gaps between strands of the manipulation wire 21 to increase manipulation resistance. As a result, the twisting characteristics of the retainer coil 201 and the manipulation wire 21 may be averaged to remove unevenness in curving characteristic.

<Hook>

Figure 17:
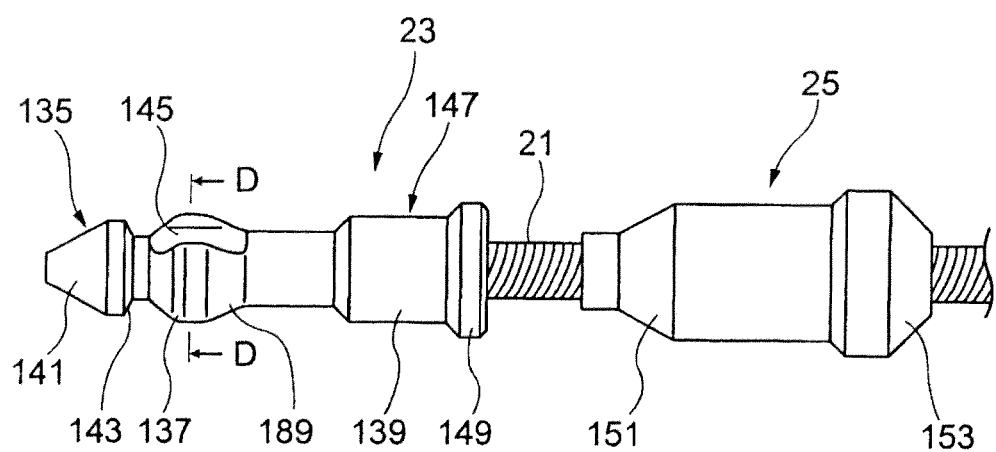
FIG. 17 is a front view of the hook and the guide bead which are fixed to the front end of the manipulation wire.
Figure 18:
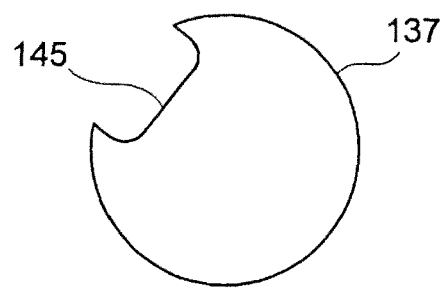
FIG. 18 is a cross-sectional view taken along line D-D in FIG. 17.

FIG. 17 is a front view of the hook 23 and the guide bead 25 fixed to the front end of the manipulation wire 21, and FIG. 18 is a cross-sectional view taken along line D-D of FIG. 17.

The hook 23 fixed to the front end of the manipulation wire 21 through soldering or laser welding is configured to have the maximum outer diameter smaller than the inner diameter of the outer fastening ring 29 (see FIG. 9) to be capable of being inserted into the outer fastening ring 29. The hook 23 has, from the front end thereof, a hook part 135, an under-head expanded-diameter part (expanded-diameter part) 137, and a rear end expanded-diameter part 139, which are integrally formed. The hook part 135 has a front end taper part (front side inclined surface) 141 and an under-head taper part (rear side inclined surface) 143 formed in this order from the front end to the rear side of the hook 23. The sectional area of the front end taper part 141 perpendicular to the axis Lo of the hook 23 (See, FIG. 44) is gradually increased from the front end to the rear side of the hook 23. And, the sectional area of the rear side inclined surface perpendicular to the axis Lo of the hook 23 (See, FIG. 44) is gradually reduced from the front end to the rear side of the hook 23. The inclined angle of the under-head taper part 143 is designed as an angle of for example, 90 degrees to 135 degrees in relation to the axial direction, and deforms the J-shaped claw parts 73 of the connection tail section 43, which is engaged with the under-head taper part 143, to control the magnitude of force when releasing the engagement. The cross-section of the hook 23 is not limited to the circular shape and may have a different shape, such as a pyramid shape or the like.

The under-head expanded-diameter part 137 has front and rear sides, each of which is formed in a taper shape, and a key recess 145 engaged with the J-shaped claw parts 73 provided in the connection tail section 43 of the clip body 27 (see FIG. 4) is formed at a portion of the outer periphery of the under-head expanded-diameter part 137. When the hook 23 and the connection tail section 43 of the clip body 27 are connected, the under-head expanded-diameter part 137 maintains the coaxiality between the hook 23 and the connection tail section 43, and secures the stability of engagement. In addition, the rear end expanded-diameter part 139 includes a small diameter part 147, and a large diameter part 149 formed at the rear end of the small diameter part 147.

<Guide Bead>

The guide bead 25 is spaced from the hook 23 in the rear side of the hook 23 and fixed to the manipulation wire 21 by soldering or laser welding. Since the hook 23 and the guide bead 25 are spaced from each other and fixed to the manipulation wire 21, the manipulation wire 21 may be curved therebetween and the degree of freedom in mutual movement may be improved. At the front end of the guide bead 25, a front end taper part 151 is formed, and at the rear end, a rear end taper part 153 is formed. The front end taper part 151 has an effect of guiding the guide bead 25 into the outer fastening ring 29 to be smoothly inserted into the outer fastening ring 29. The rear end taper part 153 has an effect of guiding the guide bead 25 to the front end sheath 15 to be smoothly accommodated in the front end sheath 15 when the clip unit 13 is pulled into the front end sheath 15.

The rear end taper part 153 is set to have a length that is exposed to the rear side from the rear end of the outer fastening ring 29 when the hook 23 and the clip unit 13 are connected. Due to this, the rear end taper part 153 can be smoothly introduced into the front end sheath 15 without causing the front end part of the front end sheath and the rear end part of the clip unit 13 to be interfered with each other even if the entirety of the clip unit 13 has completely protruded to the outside from the front end sheath.

Figure 19:
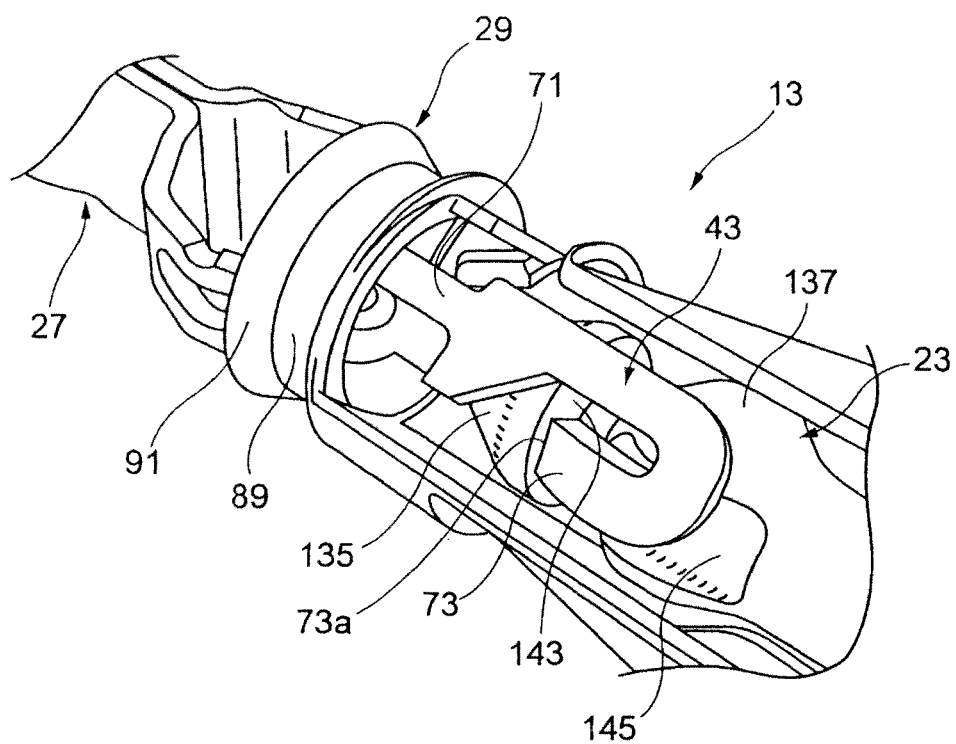
FIG. 19 is a perspective view illustrating, partially in cut-away, the clip body and the hook in the state where they are engaged with each other.

FIG. 19 is a perspective view illustrating, partially in cut-away, the clip body and the hook in the state where they are engaged with each other.

When the hook 23 and the clip unit 13 are connected, the clip body 27 is restrained in rotating position around the axial direction since the J-shaped claw parts 73 of the connection tail section 43 are engaged in the key recess 145. In addition, the front ends 73a of the J-shaped claw parts 73 are engaged with the under-head taper part 143, thereby determining the axial position of the clip body 27. In this state, since the key recess 145 is engaged with the connection tail section 43 (J-shaped claw parts 73) of the clip body 27, the torque of the manipulation wire 21 can be transmitted to the clip body 27.

<Clip Case>

Figure 20:
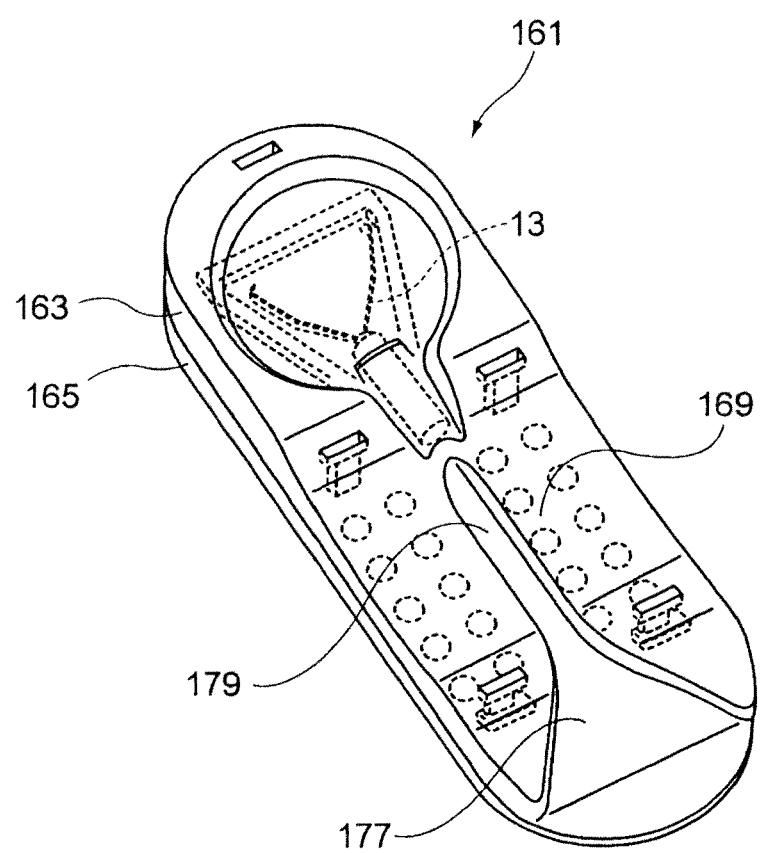
FIG. 20 is a perspective view of a clip case.

In the clip manipulation device 11 configured as described above, the clip unit 13 is mounted on the hook 23 provided at the front end of the manipulation wire 21, and a biological tissue is ligated by a pair of the arm parts of the clip unit 13. The clip unit 13 is accommodated in a clip case 161 in advance, which is illustrated in FIG. 20 as a perspective view, and the clip unit 13 is mounted on the hook 23 by inserting the hook 23 at the front end of the manipulation wire 21 into the case from the accommodated state.

Figure 21:
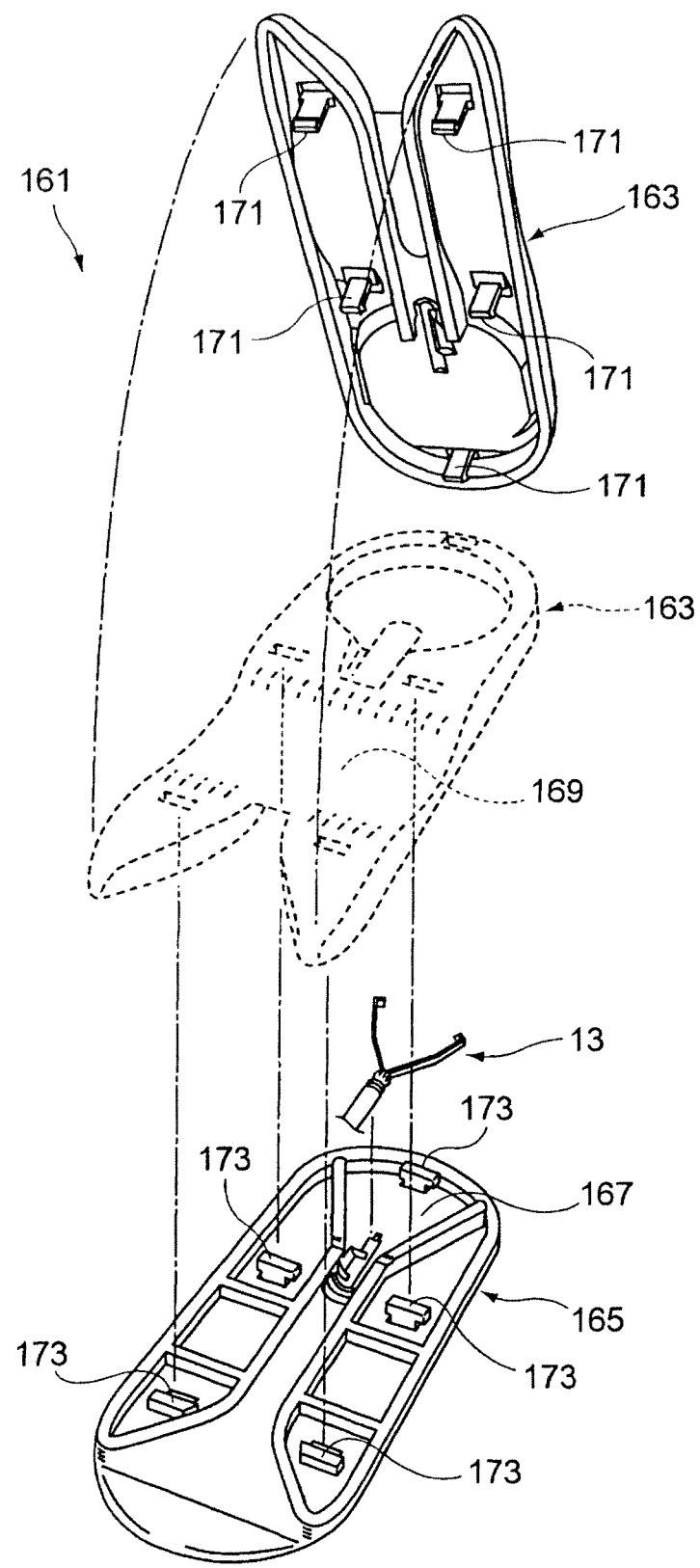
FIG. 21 is an exploded perspective view of the clip case.

An exploded perspective view of the clip case is illustrated in FIG. 21. The clip case 161 is comprised of a top case 163 and a bottom case 165, and is configured by combining the top case 163 and the bottom case 165. The clip unit 13 is located in a clip receiving chamber 167 formed between the top case 163 and the bottom case 165. The top case 163 and the bottom case 165 are integrated by engaging a plurality of engagement claws 171 formed in the top case 163 with claw engagement parts 173 formed in the bottom case 165.

Figure 22:
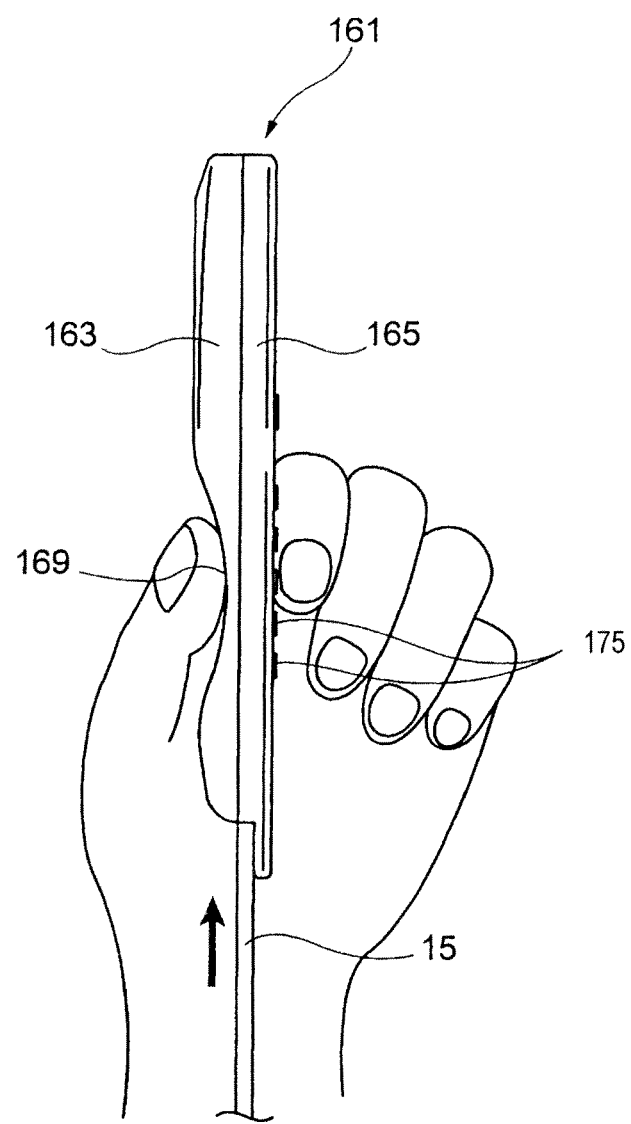
FIG. 22 is a side view of the clip case.

A side view of the clip case is illustrated in FIG. 22. The top case 163 has a sheath press part 169 narrowly formed in the thickness direction. In addition, an anti-slipping uneven pattern 175 is formed on the bottom case 165 at a position corresponding to the sheath press part 169, thereby enhancing a grip performance when the clip case 161 is grasped.

<Mounting of Clip Unit>

Figure 23:
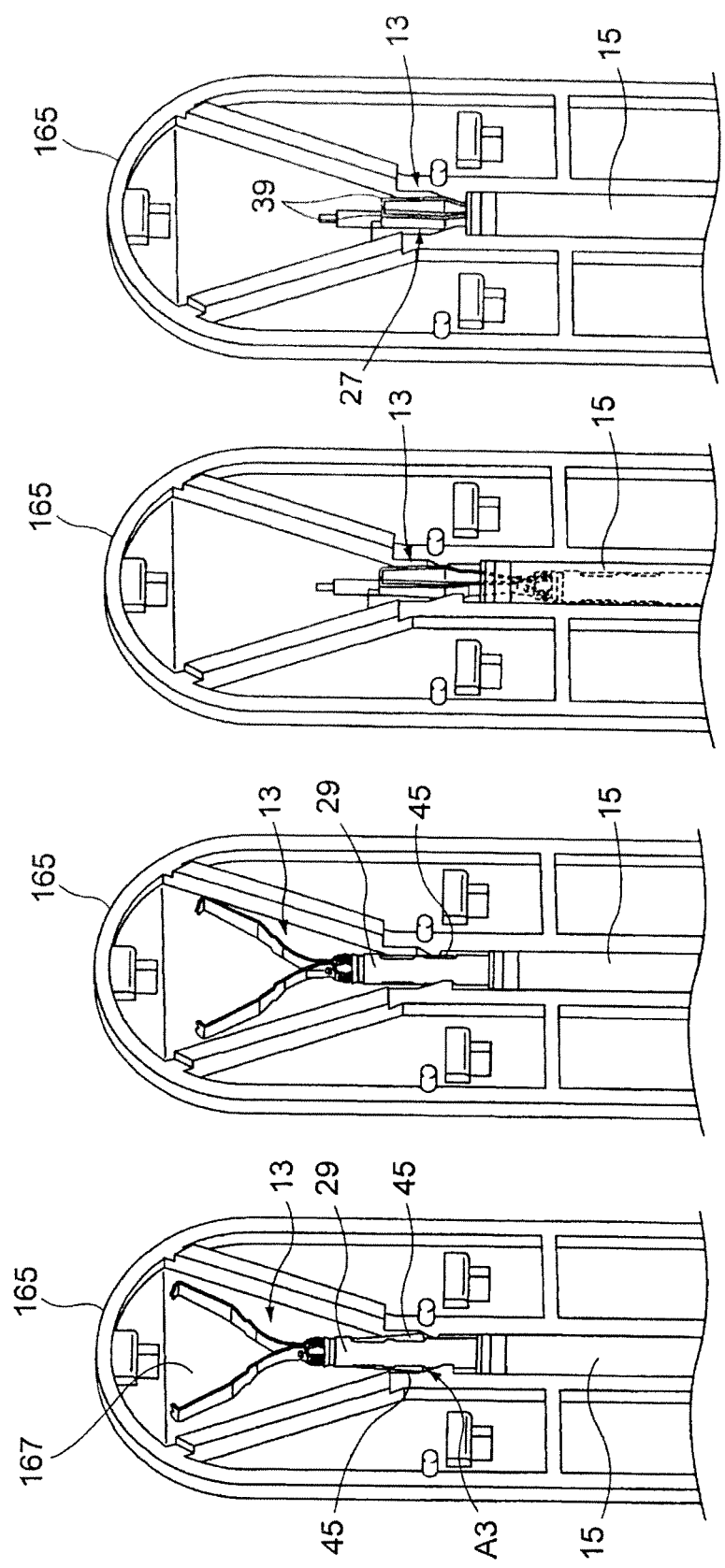
FIGS. 23A to 23D are explanatory views illustrating a sequence of mounting the clip unit of the clip case to the hook.

A sequence of mounting the clip unit of the clip case to the hook is illustrated in FIGS. 23A to 23D. As illustrated in FIG. 23A, the clip unit 13 is arranged in the clip receiving chamber 167 in advance.

In order to mount the clip unit 13 to the clip mounting device, the front end sheath 15 is firstly inserted into a sheath insertion part 179 from a sheath guide part 177 of the clip case 161, which are illustrated in FIG. 20. In addition, the front end sheath 15 is pushed into the sheath insertion part 179 until the front end of the front end sheath 15 is abutted against the end of the inside of the sheath insertion part 179. In this state, the clip case 161 is gripped in the thickness direction while pressing the front end sheath 15 against the clip case 161 as illustrated in FIG. 22.

Figure 24:
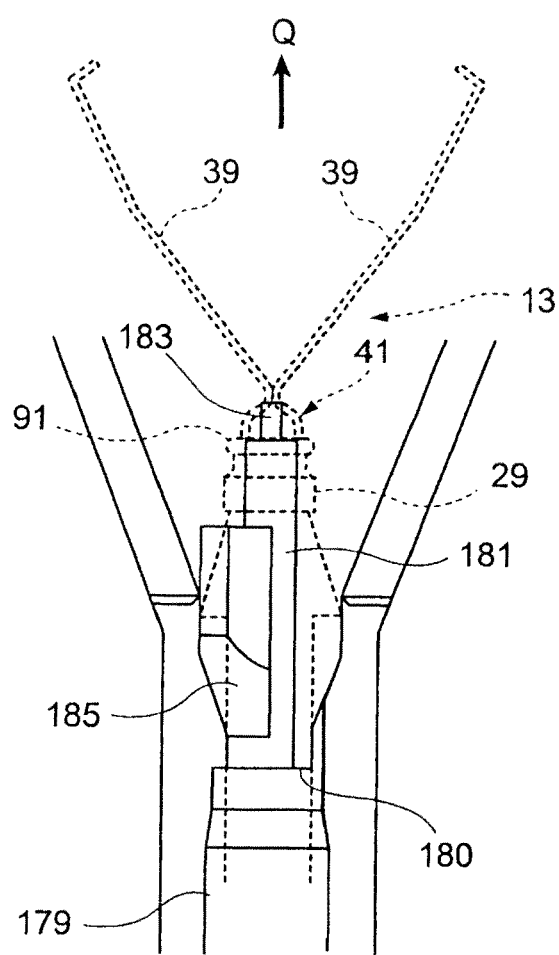
FIG. 24 is an enlarged view of the part indicated by arrow A3 in the bottom case of FIG. 23A.
Figure 25:
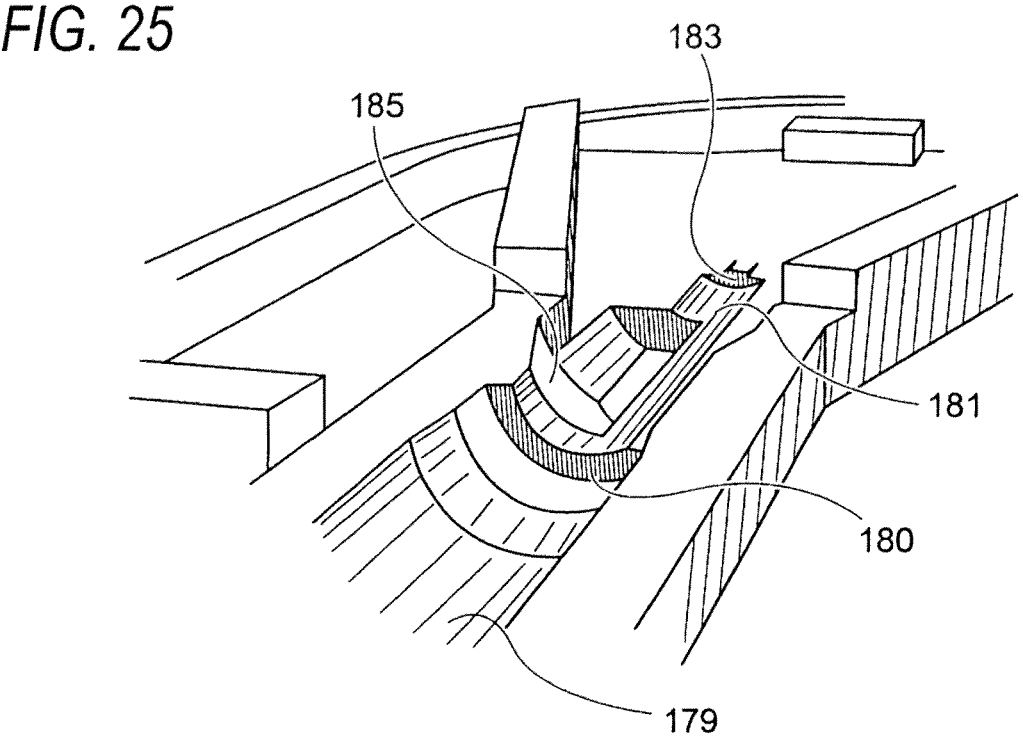
FIG. 25 is a perspective view of the part indicated by arrow A3 in the bottom case of FIG. 23A.

The part indicated by arrow A3 of the bottom case 165 in FIG. 23A is illustrated in FIG. 24 as an enlarged view and is illustrated in FIG. 25 as a perspective view, respectively.

As illustrated in FIGS. 24 and 25, the front end of the front end sheath 15 is pushed into the sheath insertion part 179 to a position where the front end abuts against the sheath abutting part 180. Then, the outer fastening ring 29 is positioned such that the taper section 91 of the front end abuts against a fastening ring abutting part 183 in a state where the outer fastening ring 29 is laid in a fastening ring retaining part 181 of a concavely curved shape. As a result, the clip unit 13 is prevented from getting out in the direction indicated by arrow Q in FIG. 24. That is, even if a forward pushing force is applied to the clip unit 13 by inserting the hook, the relative position of the clip unit 13 and the clip case 161 is not changed. For this reason, the clip unit 13 is prevented from coming into contact with and being damaged by the clip case 161.

Since the outer periphery of the outer fastening ring 29 is retained in the fastening ring retaining part 181 corresponding to the outer periphery, the outer fastening ring 29 is precisely retained within the clip case 161, and the outer fastening ring 29 may be arranged without axial deviation. Therefore, the front end part of the front end sheath 15 and the rear end part of the outer fastening ring 29 will not interfere with each other when the front end sheath 15 is inserted into the clip case 161.

In addition, the flap parts 45 of the inner fastening ring 31 come into contact with the flap guide taper part 185 such that the clip unit 13 laid in the clip case 161 is biased to the base end side not to be disengaged. As a result, the clip unit 13 will not escape from the clip case 161 by the self-weight of the clip unit 13, vibration at the time of transportation, and handling of the clip case.

Figures 26A, 26B, 26C:
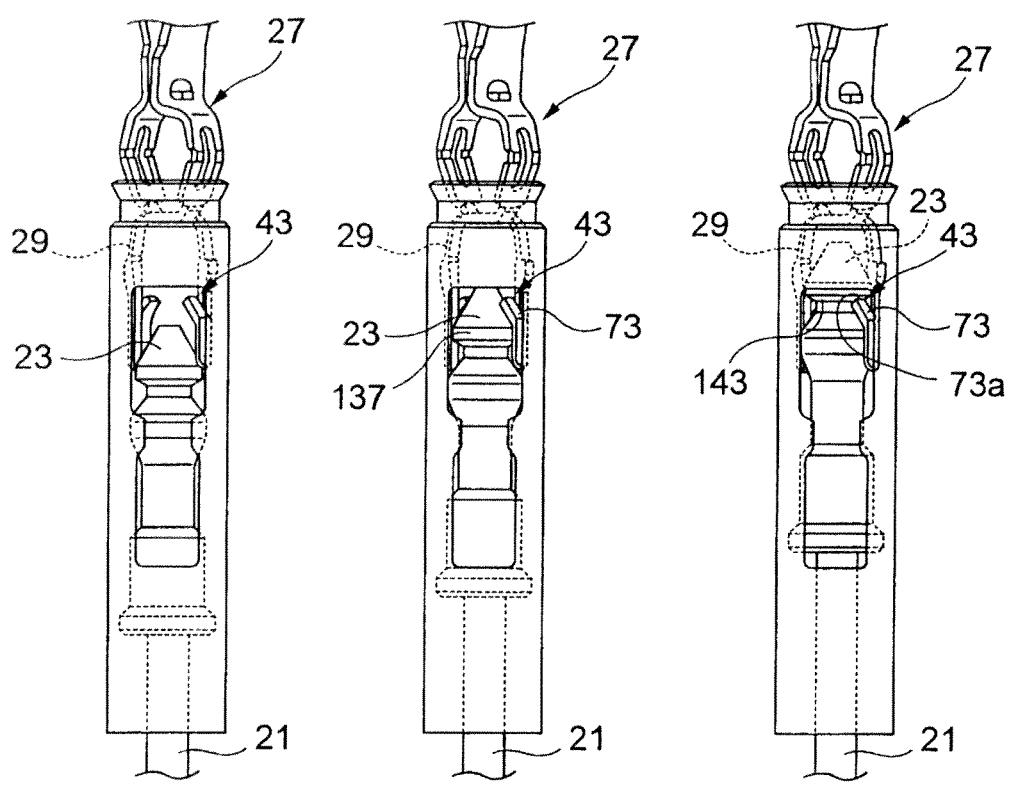
FIGS. 26A to 26C are explanatory views illustrating the hook from the state where the hook is inserted into the connection tail section of the clip body to the state where the hook is connected to the connection tail section in a step-by-step manner.

Then, the slider 35 of the handle manipulation unit 17 is moved forward, and the manipulation wire 21 is extended, so that the hook protrudes to the outside from the front end of the front end sheath 15. FIGS. 26A to 26C are explanatory views illustrating the hook from the state where it is inserted into the connection tail section 43 of the clip body 27 to the state where it is connected to the connection tail section 43 in a step-by-step manner. The hook 23 starts to be engaged with the connection tail section 43 as illustrated in FIG. 26A, then the J-shaped claw parts 73 are moved to pass the under-head expanded-diameter part 137 of the hook 23 as illustrated in FIG. 26B, and then the front ends 73a of the J-shaped claw parts 73 are engaged with the under-head taper part 143 of the hook 23 as illustrated in FIG. 26C, thereby completing the connection between the hook 23 and the clip body 27.

Figure 27:
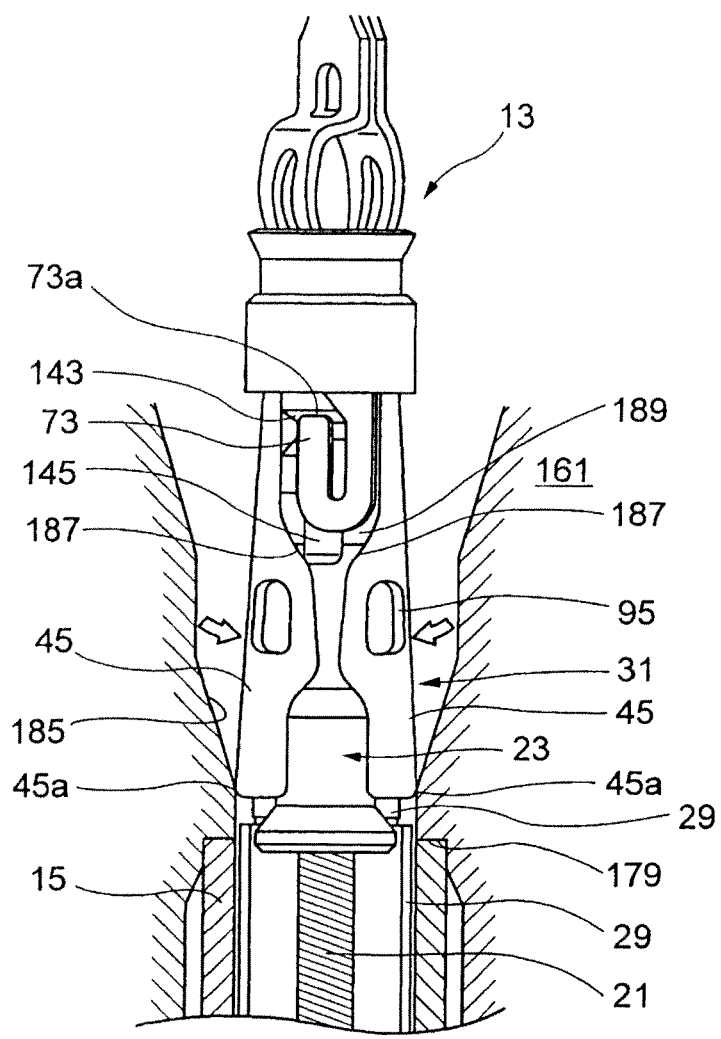
FIG. 27 is an enlarged explanatory view illustrating the flap parts in the state of being closed.

Next, the slider 35 of the handle manipulation unit 17 is moved backward to pull the manipulation wire 21 backward. As such, as illustrated in FIG. 23B, the flap parts 45 extending radially outward from the outer fastening ring 29 are closed. FIG. 27 is an enlarged explanatory view illustrating the flap parts while they are being closed. When the manipulation wire 21 is pulled backward, the front ends 73a of the J-shaped claw parts 73 are abutted against the under-head taper part 143 of the hook part 135, whereby the pulling force is transmitted to the clip unit 13. When the clip unit 13 is pulled out to the base end side in relation to the clip case 161, the free ends 45a of the flap parts 45 abut against the flap guide taper part 185 of the clip case 161, thereby gradually reducing the opening extent, and finally closing the opening to the extent of the outer diameter of the outer fastening ring 29.

When the free ends 45a of the flap parts 45 are closed to the outer diameter of the outer fastening ring 29, the clip unit 13 is inserted into the front end sheath 15 as illustrated in FIG. 23C. The force at the time of closing the flap parts 45 is set to be sufficiently smaller than that for deforming and introducing the loop parts 47 of the base end section 41 (see FIG. 4) of the clip body 27 into the outer fastening ring 29. For this reason, the flap parts 45 are securely closed.

In addition, when the flap parts 45 are closed, hook abutments 187 of the flap parts 45 abut against a flap abutting taper part 189 of the hook 23. Due to this abutting of the hook abutments 187, the relative movement between the hook 23 and the inner fastening ring 31 is restrained, and the reciprocating movement by the manipulation wire 21 in the axial direction may be directly transmitted to the inner fastening ring 31. That is, the position for transmitting force from the hook 23 to the clip unit 13 after the flap parts 45 are closed is changed from the engagement position of the J-shaped claw parts 73 and the under-head taper part 143 of the hook 23 to the engagement position of the hook abutments 187 and the flap abutting taper part 189 of the hook 23.

When the manipulation wire 21 is pulled backward, the clip unit 13 is stored in the front end sheath 15 as illustrated in FIG. 23D. When the clip unit 13 is stored, the arm parts 39 of the clip body 27 are guided to the ring part 77 of the inner fastening ring 31 (see FIG. 6) and inserted into the front end sheath 15 while being closed.

As such, the clip unit 13 is mounted to the clip manipulation device 11 illustrated in FIG. 1.

<Manipulation for Ligation>

Next, manipulation for ligating a biological tissue by the ligation device 100 illustrated in FIG. 1 will be described.

(Insertion of Sheath into Forceps Channel)

Figure 28A:
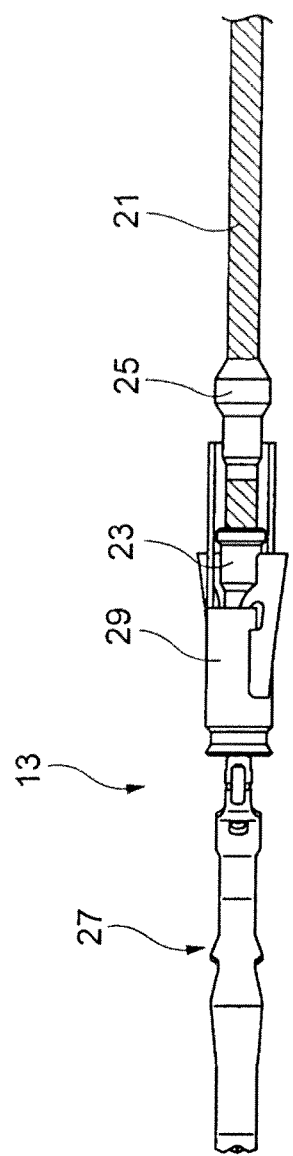
FIG. 28A is an explanatory view illustrating a state where the clip body and the outer fastening ring are connected with each other.
Figure 28B:
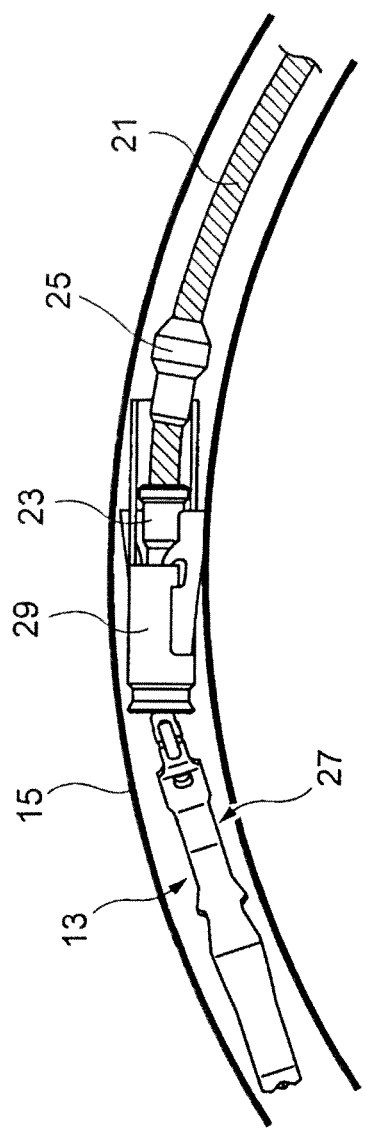
FIG. 28B is an explanatory view illustrating the front end sheath curved in the connected state of FIG. 28A.

An operator of an endoscope inserts the front end sheath 15 into a forceps channel which is a treatment instrument insertion passage of the endoscope in a state where the clip unit 13 is stored in the front end sheath 15 of the ligation device 100. In such a case, the connected form of the clip body 27 and the outer fastening ring 29 is changed to a curved state illustrated in FIG. 28B by following the curve of the front end sheath 15 from the linear state illustrated in FIG. 28A. Since the hook 23 and the guide bead 25 are spaced from each other and fixed to the manipulation wire 21, the manipulation wire 21 can be curved between the hook 23 and the guide bead 25, and the degree of freedom in mutual movement can be enhanced.

The outer fastening ring 29 is formed from a hard metal material. For this reason, the longitudinal length of the outer fastening ring 29 determines the facilitation of insertion in relation to the endoscope, and it is desirable that the entire length of the outer fastening ring 29 is short.

Figure 29:
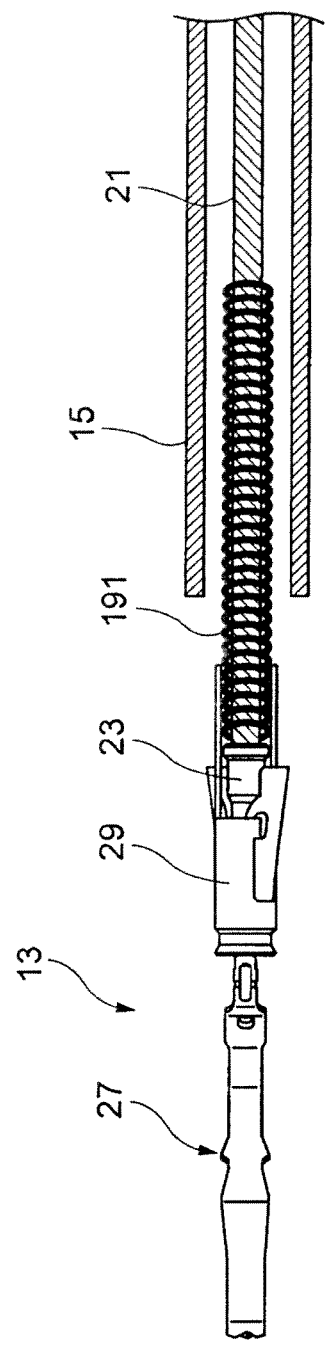
FIG. 29 is an explanatory view illustrating a configuration example in which the guide bead is replaced by a guide spring.

As illustrated in FIG. 29, the guide bead 25 may be replaced by a guide spring 191 arranged to the outside of the manipulation wire 21 in the rear side of the outer fastening ring 29. By setting the guide spring 191 is a length that makes the rear end of the guide spring 191 be always inserted into the front end sheath 15 in the entire stroke area of the reciprocating movement of the manipulation wire 21 in the axial direction, it is possible to secure the following performance for curving and a guidance performance to the front end sheath 15.

Figure 30:
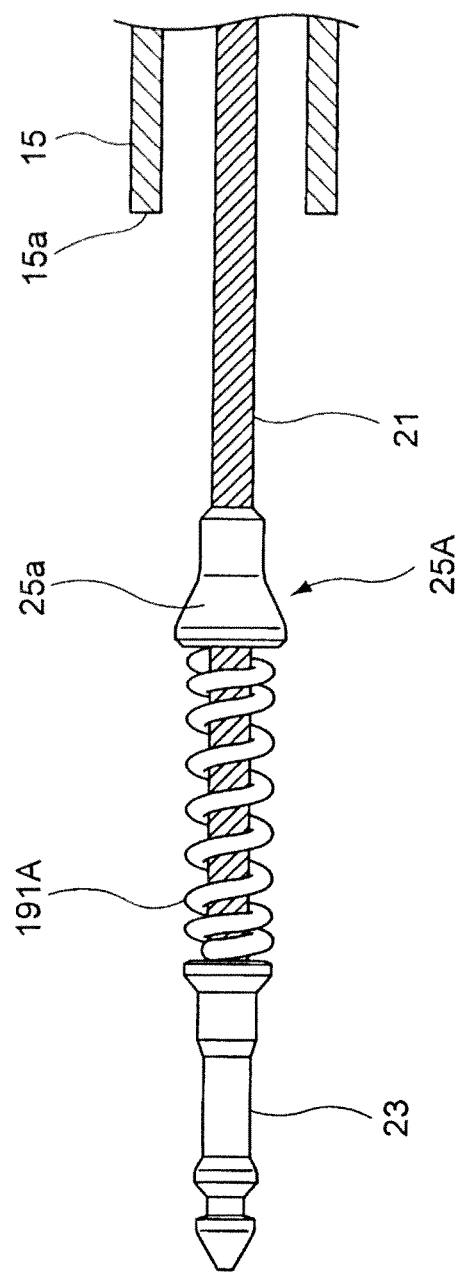
FIG. 30 is an explanatory view illustrating a configuration example in which a guide bead is arranged at the rear end of the guide spring.

As illustrated in FIG. 30, a guide bead 25A having a rear end taper part 25a may be provided at the rear end of the guide spring 191A. The guide bead 25A is fixed to the manipulation wire 21 by soldering or welding. The guide spring 191A is arranged to be free between the hook 23 and the guide bead 25A without being biased. With this arrangement, even if the guide spring 191A is set in a length that makes the rear end thereof project from the front end sheath 15, the rear end of the guide spring 191A can be introduced into the front end sheath 15 without interference between the front end 15a of the front end sheath 15 and the guide spring 191A. Accordingly, the following performance for curving and the guidance performance to the front end sheath 15 can be secured and the entire length of the guide spring 191A can be set shortly. Therefore, the flexibility can be further enhanced.

(Clip Protrusion from Front end sheath)

FIGS. 31A to 31F illustrate the arm parts of the clip unit until they are expanded from the front end sheath.

Figure 31A:
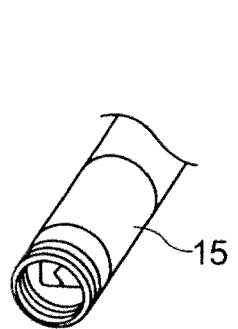
FIGS. 31A to 31F are explanatory views illustrating states where the arm parts of the clip unit are expanded from the front end sheath.
Figure 31D:
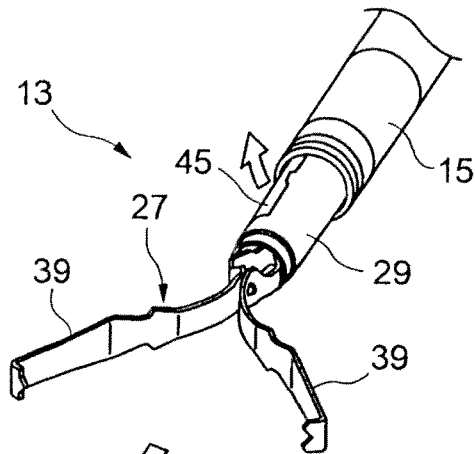
Figure 31B:
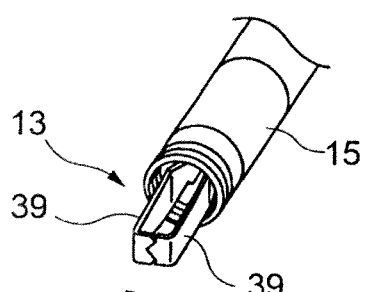

As illustrated in FIG. 31A, the clip unit 13 protrudes to the outside from the front end of the front end sheath 15 by continuously feeding the manipulation wire toward the front side by manipulation from the handle manipulation unit in the state where the clip unit is accommodated in the front end sheath 15. FIG. 31B illustrates the clip unit 13 when the arm parts 39 start to protrude from the front end sheath 15.

Figure 31E:
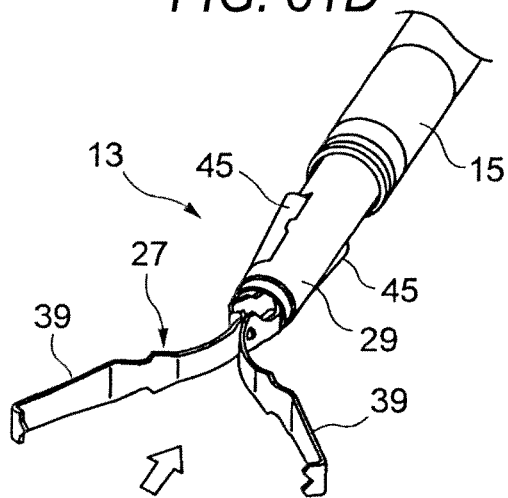
Figure 31C:
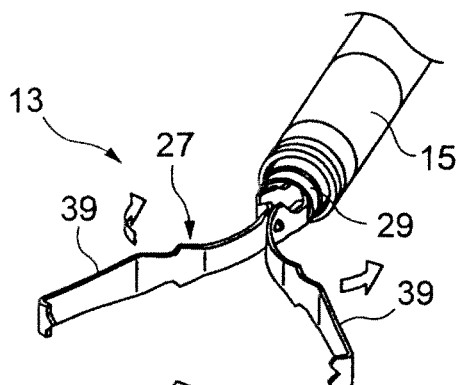

When the clip unit 13 protrudes to the outside from the front end sheath 15, the arm parts 39 are gradually expanded as illustrated in FIG. 31C. Then, when the flap protruding holes 93 of the outer fastening ring 29 completely get out of the front end sheath 15 as illustrated in FIG. 31D, the flap parts 45 are elastically returned from the flap protruding holes 93 and hence individually opened diametrically outward. The flap parts 45 are maintained at a predetermined opening angle where each of the flap opening prevention taps 95 is engaged with one side 85a of each one of the flap locking holes 85 (see FIG. 11).

Figure 31F:
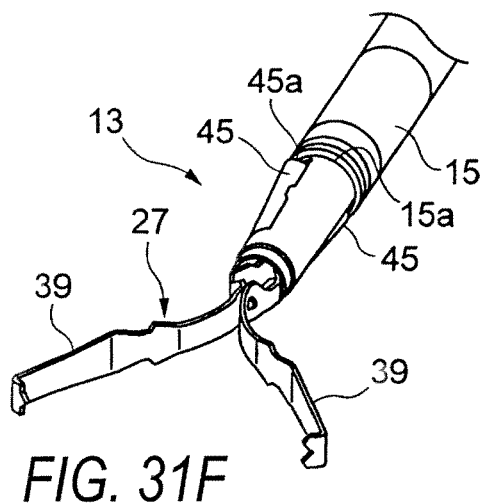

Then, as illustrated in FIG. 31E, the clip unit 13 further protrudes from the front end sheath until the flap parts 45 are certainly opened, and as illustrated in FIG. 31F, the clip unit 13 is returned to the rear side by pulling the manipulation wire to the base end side. At this time, the free ends 45a of the flap parts 45 are stopped at a position where they abut against the front end 15a of the front end sheath 15.

That is, the flap parts 45 function as a stopper for defining the axial positions of the clip unit 13 and the front end sheath 15. The diametrically outward opening angle of the flap parts 45 is determined by the designed sizes of the outer fastening ring 29 and the inner fastening ring 31 and is constant since it is not varied depending on the front end sheath 15. For that reason, even if the clip unit 13 and the front end sheath 15 are deviated or inclined in relation to the axis, the free ends 45a of the flap parts 45 certainly abut against the front end 15a of the front end sheath 15 to function as a stopper at a correct position since the flap parts 45 are opened with high precision at the designed opening angle. Accordingly, it is possible to always correctly position the clip unit 13 in relation to the front end sheath 15 to axially coincide with the front end sheath 15, and the subsequent ligation action can be smoothly and reliably performed.

(Opening/closing Action of Arm Parts)

Next, the opening/closing action of the arm parts for gripping a biological tissue will be described.

FIGS. 32A to 32E illustrate the actions of the arm parts of the clip unit, from expanding after having protruded to the outside from the front end sheath to ligating a biological tissue, in a step-by-step manner.

Since the arm parts 39 of the clip body 27 are closed when the clip unit 13 stored in the front end sheath 15, the clip unit 13 tends to be closed, thereby reducing the opening angle. The plastic deformation of the base end section 41 may compensate for the reduction of the opening angle.

When the base end section 41 of the clip body 27 illustrated in FIG. 32A is inserted into the constricted spot 89 of the outer fastening ring 29 by being pulled by the manipulation wire, the loop parts 47, 47 are gradually narrowed as illustrated in FIG. 32B, and hence the base end section 41 is plastically deformed. That is, the outer diameter of the base end section 41 of the clip body 27 is larger than the inner diameter DS (see FIG. 9) in the major axis side in the constricted spot 89 of the outer fastening ring 29. For this reason, when the base end section 41 of the clip body 27 is pulled into the outer fastening ring 29, the loop parts 47, 47 of the base end section 41 are pressed and deformed from the opposite sides thereof.

As the loop parts 47, 47 of the base end section 41 are deformed, the arm parts 39, 39 of the clip body 27 perform expansion movement using a deviation prevention claw 51 as a fulcrum point. Accordingly, as illustrated in FIG. 32B, the arm parts 39, 39 are widely expanded as illustrated to have an opening size that is capable of gripping a sufficient amount of tissue.

Figure 33B:
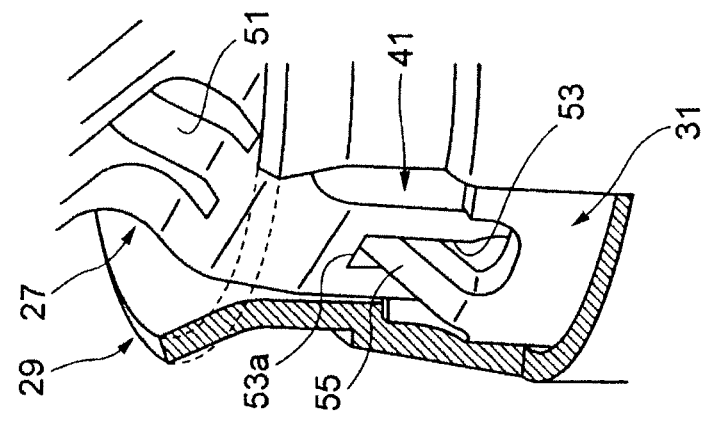
FIG. 33B is an explanatory view illustrating the appearance of the expansion retaining protrusion abutting against the front end of the slit part.
Figure 33A:
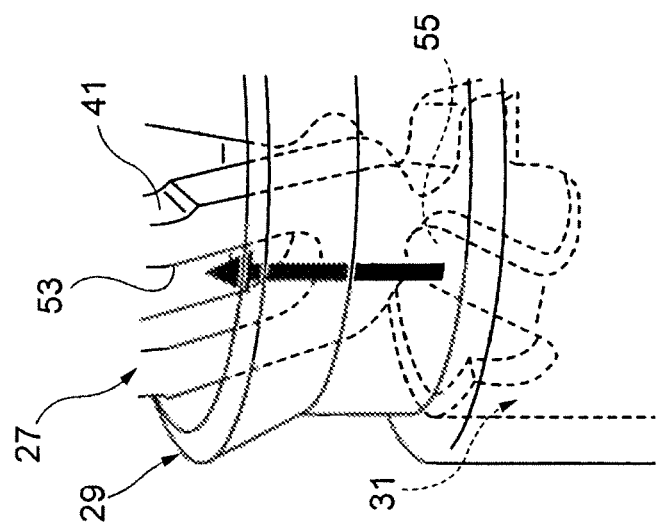
FIG. 33A is an explanatory view illustrating the appearance of an expansion retaining protrusion of the inner fastening ring entering into the slit part in the base end section.

The timing of expanding the arm parts 39, 39 is transmitted to an operator as timing when a resistance against the pulling of the manipulation wire has occurred. That is, an expansion retaining protrusion 55 of the inner fastening ring 31 illustrated in FIG. 33A is introduced into the slit part 53 formed in the base end section 41 of the clip body 27 as the base end section 41 is moved to the base end side (downward in the drawing) by pulling the manipulation wire. When the manipulation wire is pulled again, the expansion retaining protrusion 55 abuts against the front end part 55a of the slit part 53, thereby producing a resistance against the pulling of the manipulation wire as illustrated in FIG. 33B.

With the resistance, the operator may readily recognize that the arm parts 39, 39 are opened at their maximum, and may temporarily stop the pulling operation of the manipulation wire in the state where the arm parts 39, 39 are opened at their maximum.

(Rotation of Clip)

Figure 34:
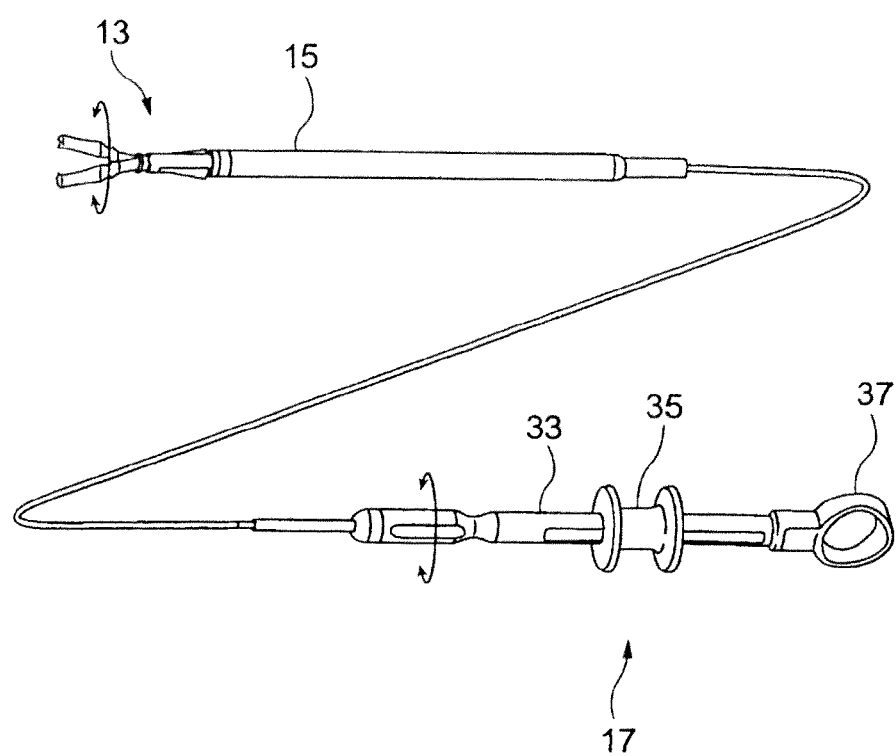
FIG. 34 is an explanatory view illustrating a rotation operation of the manipulation unit body in relation to the finger pull ring.

As illustrated in FIG. 32C, the operator moves the clip unit 13 mounted in the front end sheath to a treatment position within a body cavity in the state where the arm parts 39, 39 are kept expanded. Then, the clip unit 13 is rotated according to a treatment direction. As described above, the rotation of the clip unit is performed by rotating the manipulation unit body 33 illustrated in FIG. 34 around the axis (Starting of Ligation)

Next, as illustrated in FIG. 32C, the operator sets the arm parts 39, 39 to a target treatment position (an affected area 195), and pulls the slider 35 of the handle manipulation unit 17 (see FIG. 34) to the rear side, i.e., to the finger pull ring 37 side. Accordingly, as illustrated in FIG. 32D, the arm parts 39, 39 are closed, and the affected area 195 is gripped. At this time, the bent linear plate parts 57 of the arm parts 39, 39 (see FIG. 4) slidably contact with the inner diameter areas of the major axis (DL) side in the constricted spot 89 of the outer fastening ring 29 (see FIG. 9), and hence the ligation action of the clip is performed.

At this time, in the base end section 41 of the clip body 27 illustrated in FIG. 33, the expansion retaining protrusion 55 formed in the slit part 53 is plastically deformed, so that the engagement between the clip body 27 and the inner fastening ring 31 is released. The expansion retaining protrusion 55 is set to be plastically deformed by a force in the extent of 10 N to 20 N, and the engagement with the inner fastening ring 31 may be readily released with the force applied when gripping the affected area 195 with the arm parts 39, 39.

As a result, the clip body 27 is made to be movable backward again, and by retracting the slider 35 to the finger pull ring 37, the clip body 27 is inserted into the outer fastening ring 29 as illustrated in FIG. 32E.

(Ligation State)

Figure 35:
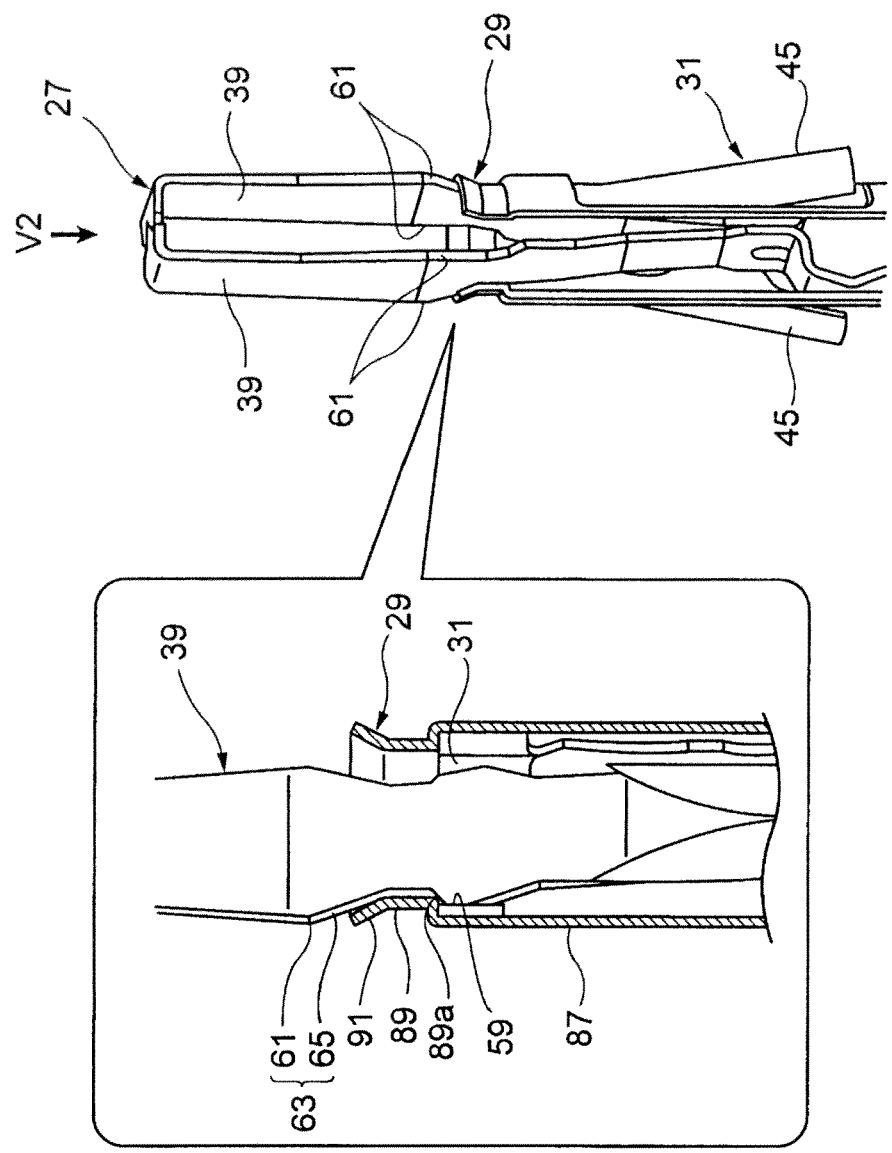
FIG. 35 is an explanatory view illustrating a disengagement prevention protrusion of an arm part locked by a stepped part formed by a constricted spot of the outer fastening ring.

When the arm parts 39, 39 are completely closed, a disengagement prevention protrusion 59 formed widely on a portion of each of the arm parts 39 is locked at the stepped part 89a formed by the constricted spot 89 of the outer fastening ring 29 as illustrated in FIG. 35. As a result, it is possible to prevent the clip body 27 from coming out to the front side of the outer fastening ring 29, and the ligation state by the arm parts 39, 39 will be retained.

In addition, when the clip body 27 is moved backward (downward in the drawing), the taper part 65 of the arm parts 39 and the pull-in prevention protrusions 61 abut against the inner diameter areas of the minor axis DS side of the constricted spot 89 (see FIG. 9), so that the clip body 27 cannot be further pulled into the outer fastening ring 29.

Figure 36:
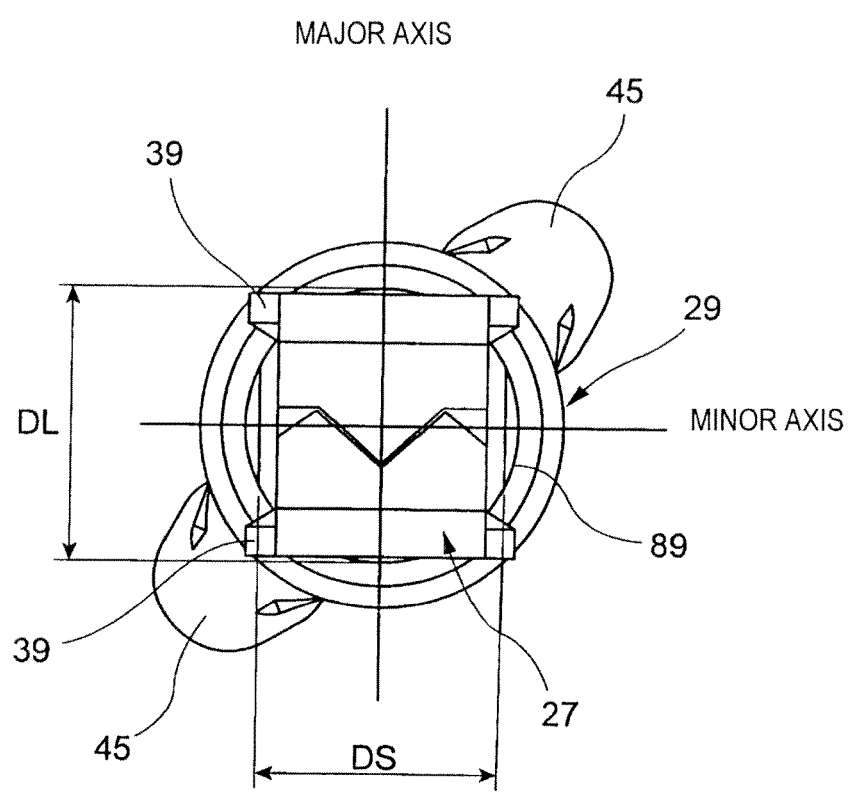
FIG. 36 is a view shown in the direction indicated by arrow V2 in FIG. 35.

FIG. 36 illustrates a view shown in the direction indicated by arrow V2 in FIG. 35.

As described above, the shape the inside of the constricted spot 89 is formed in an oval shape, in which the diameter of the major axis DL and the diameter of the minor axis DS are different from each other. The major axis of the constricted spot 89 is set to coincide with the expansion direction of the arm parts 39, 39 of the clip body 27. Due to this, the constricted spot 89 abuts against the loop parts 47, 47 of the base end section 41 (see FIG. 4) to control the expansion extent of the pair of arm parts 39. In addition, the minor axis of the constricted spot 89 is set to be parallel to the widthwise direction of the each of the pull-in prevention protrusions 61 on the arm parts 39, 39. Due to this, when the clip body 27 is accommodated in the outer fastening ring 29, the constricted spot 89 engaged with the pull-in prevention protrusions 61 to control the pull-in extent of the clip body 27.

(Release of Clip Unit)

Figure 37:
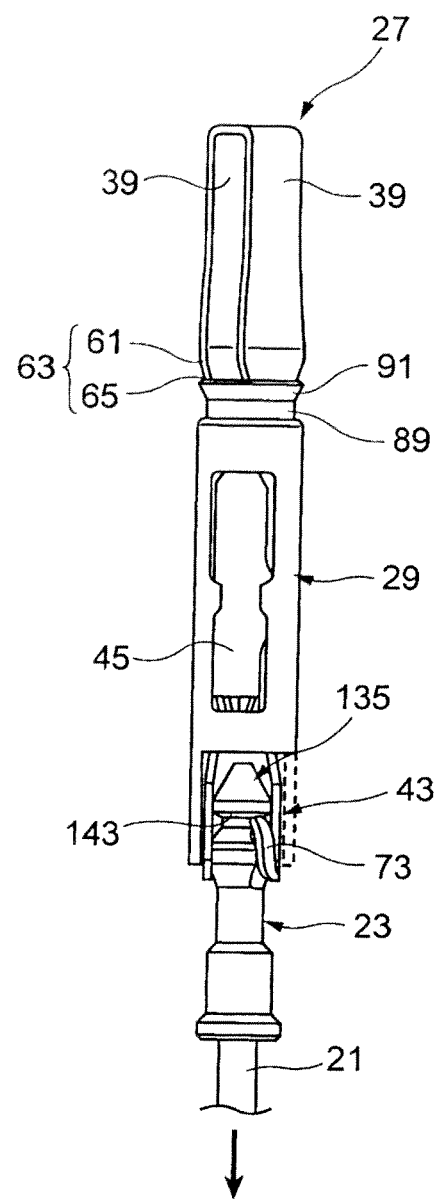
FIG. 37 is an explanatory view illustrating, partially in cut-away, the clip unit in the state where the clip unit has completed the ligation.

FIG. 37 illustrates, partially, in cut-away, the clip unit in the state where the clip unit has completed ligation.

If the pulling force of the hook 23 is further increased in the state where the pull-in prevention protrusions 61 formed on the arm parts 39 of the clip body 27 and the constricted spot 89 of the outer fastening ring 29 are engaged with each other, a tensile force is also applied to the engagement part between the hook 23 and the connection tail section 43 of the clip body 27.

Figures 38A, 38B:
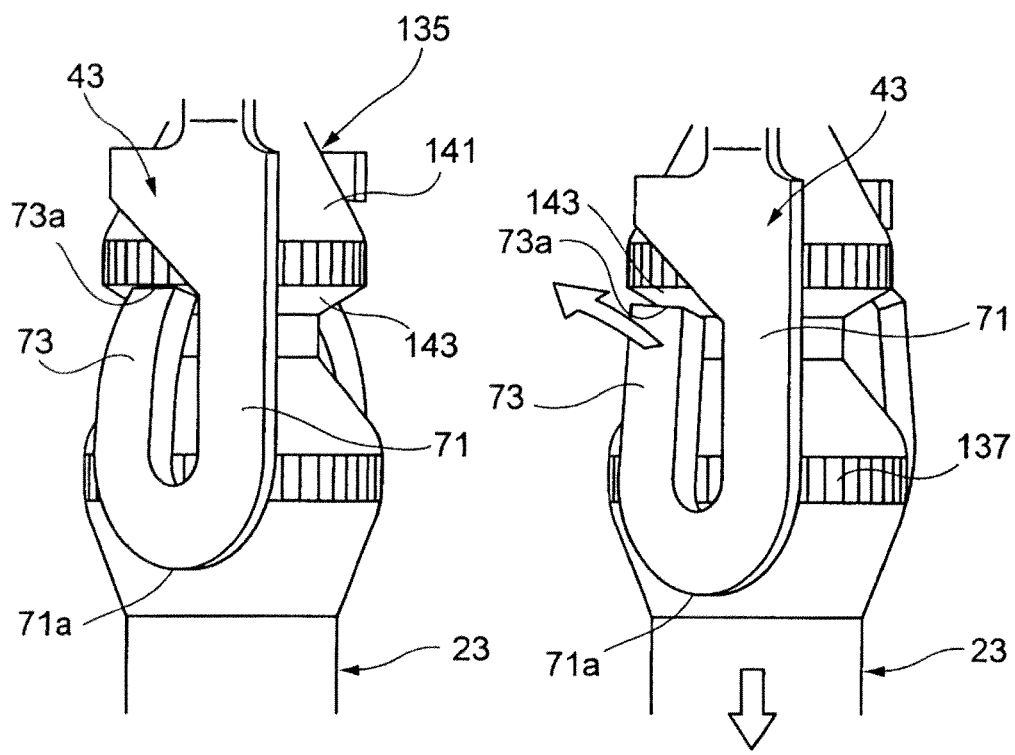
FIGS. 38A and 38B are explanatory views illustrating the hook and the connection tail section in the state where the hook and the connection tail section are engaged with each other, and in the state where the hook and the connection tail section is started to be disconnected, respectively.

FIG. 38A illustrates the hook and the connection tail section in the engaged state, and FIG. 38B illustrates the hook and the connection tail section in the state of starting to release the engagement. As illustrated in FIG. 38A, the hook part 135 of the hook 23 is positioned such that the front ends 73a of the J-shaped claw parts 73 of the connection tail section 43 abut against the under-head taper part 143 formed on the rear side from the largest outer diameter area of the front end taper part 141. When the hook 23 is returned backward in relation to the connection tail section 43, the J-shaped claw parts 73 are forcibly spread diametrically outward, thereby releasing the engagement with the under-head taper part 143 as illustrated in the FIG. 38B.

FIGS. 39A to 39C illustrate a process of releasing the J-shaped claw parts from the engagement in a step-by-step manner.

As illustrated in FIG. 39A, when the hook 23 is returned backward from the state in which the front ends 73a of the J-shaped claw parts 73 of the connection tail section 43 abut on the under-head taper part 143, the front ends 73a of the J-shaped claw parts 73 are expanded diametrically outward while being slid on the under-head taper part 143. In addition, when the front ends 73a of the J-shaped claw parts 73 are spread diametrically outward over the maximum outer diameter of the hook part 135 as illustrated in FIG. 39B, the hook 23 is disengaged from the connection tail section 43 and the engagement of the hook 23 and the connection tail section 43 is released as illustrated in FIG. 39C.

Due to this, it is possible to retract the clip manipulation device within a body cavity in the state where the clip unit that has ligated a biological tissue such as an affected area is detained in the body cavity.

<Examples of Other Configurations of Clip Body>

FIGS. 40A and 40B and FIGS. 41A and 41B illustrate different examples of configuration of the connection tail section 43, respectively.

Figure 40A:
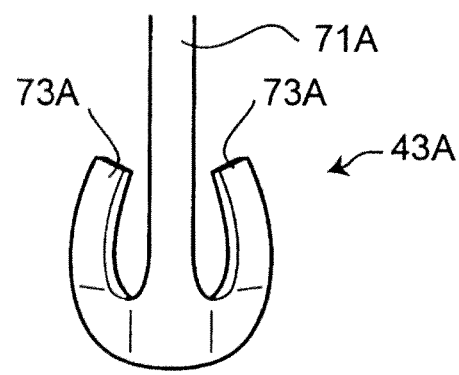
FIG. 40A is a partial configuration view of a connection tail section formed with a pair of engagement claw parts.
Figure 40B:
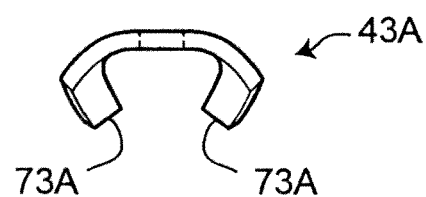
FIG. 40B is a bottom view of FIG. 40A.

FIG. 40A is a partial configuration view of a connection tail section formed with a pair of engagement claw parts 73A, 73A, and FIG. 40B is a bottom view of FIG. 40A. In this example of configuration, the pair of the engagement claw parts 73A, 73A are provided respectively to extend toward the front side with reference to the rear end 71a of the arm 71A. The engagement claw parts 73A, 73A are inwardly inclined toward the central axis of the hook accommodated by the connection tail section 43A as illustrated in FIG. 40B.

With this arrangement, the engagement claw parts 73A, 73A abut against the rear inclined surface of the hook, whereby the connection strength between the clip unit and the hook can be increased. In addition, the number of the engagement claw parts is not limited two, and three or more engagement claw parts may be provided In addition, since the loads from the engagement claw parts 73A, 73A are uniformly applied and the bending moment applied to the part 71A is reduced, it is possible to increase the connection strength.

Figure 41A:
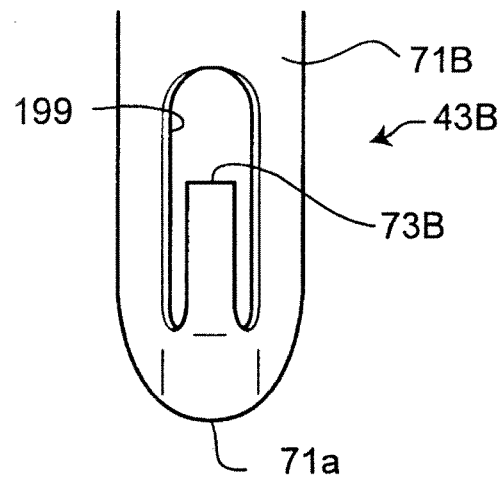
FIG. 41A is a partial configuration view of a connection tail section with an engagement claw part arranged in an opening formed in an arm part.
Figure 41B:
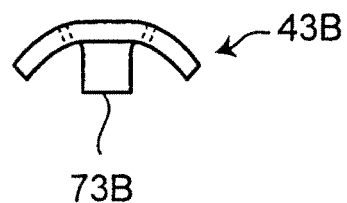
FIG. 41B is a bottom view of FIG. 41A.

FIG. 41A illustrates a partial configuration view in which an engagement claw part is arranged in an opening formed in an arm 71B, and FIG. 41B is a bottom view of FIG. 41A. In this example of configuration, an opening 199 is formed in the vicinity of the rear end 71a of the arm 71B, and an engagement claw part 73B is provided in the opening 199 to extend from the rear end 71a side of the opening 199 to the front side. The engagement claw part 73B is inclined inwardly toward the central axis of the hook to the same with the above-described claw parts.

With this arrangement, the engagement claw part 73B may be simply configured. As a result, it is easy to fabricate and assemble.

Figure 42:
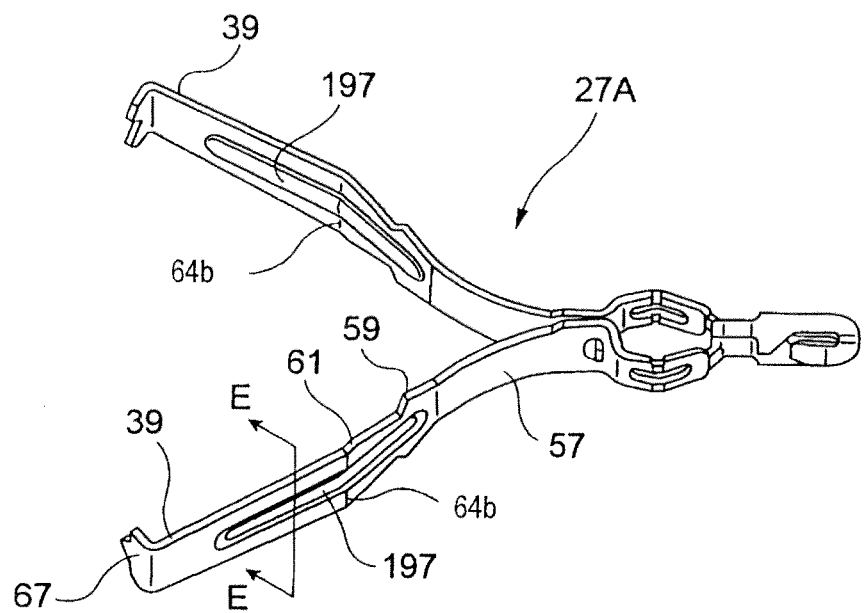
FIG. 42 is an explanatory view illustrating a construction in which a reinforcement rib is provided to extend in the longitudinal direction of each of the arm parts with a bending point of the arm part as the center.

The above-described clip body 27 may be formed by bending a flat metallic plate, and a large force is applied to the arm parts 39, 39 at the time of ligation. Therefore, as illustrated in FIG. 42, a clip body 27A is formed with reinforcement ribs 197, 197 extending in the longitudinal direction with the second bending points 64b as the centers, respectively, to increase the strength of the clip body 27A. The reinforcement ribs 197, 197 are formed to bulge on the inner sides which the pair of the arm parts 39, 39 are opposite to each other.

Figure 43:
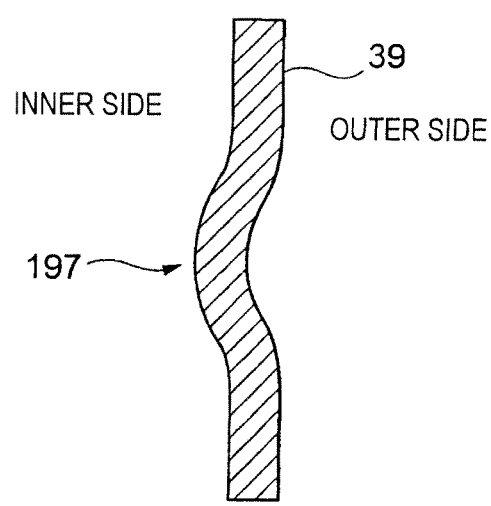
FIG. 43 is a cross-sectional view taken along line E-E of FIG. 42.

FIG. 43 is a cross-sectional view taken along line E-E of FIG. 42. Each of the reinforcement ribs 197 is formed by pressing an arm part 39 in the thickness direction of the plate. Since the strength of the clip body 27 is increased by providing the reinforcement ribs 197, 197, a stronger ligation may be performed for a biological tissue, and the arm parts may be formed more narrowly to miniaturize the clip body.

<Other Example of Configuration of Flap Parts>

Next, another example of configuration will be described in which the flap parts of the clip unit 13 are expanded in the diametrically outward direction of the fastening ring 26 to abut against the front end of the front end sheath 15, thereby positioning the clip unit 13 in relation to the front end sheath 15.

Figure 44:
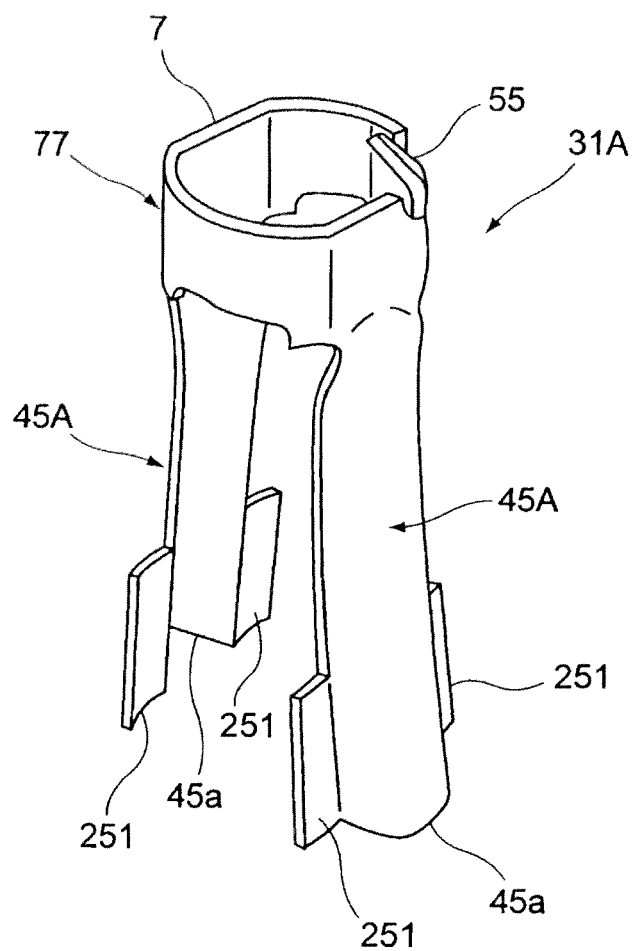
FIG. 44 is a perspective view of an inner fastening ring of another example of configuration.

FIG. 44 is a perspective view illustrating another example of the inner fastening ring. The parts common to those illustrated in FIGS. 6A to 6C will be denoted by the same reference numerals, and the description thereof will be omitted or simplified. Like the configuration illustrated in FIGS. 6A to 6C, an inner fastening ring 31A includes a pair of flap parts 45A, 45A, each of which is cantilevered on the ring part 77 of the inner fastening ring 31A and extends along the longitudinal axis of the inner fastening ring 31A. The free ends 45a of the flap parts 45A are elastically biased in the diametrically outward direction of the inner fastening ring 31A.

An outer fastening ring combined with the inner fastening ring 31A on the same axis has a configuration where the flap opening prevention taps 95 are not provided at a pair of longer sides 93a of the flap protruding hole 93, which is the same with the outer fastening ring 29 illustrated in FIGS. 9A and 9B.

Each of the flap parts 45A, 45A of the inner fastening ring 31A has a circular arc shape when it is viewed in a cross-section lying at right angles to the longitudinal axis of the inner fastening ring 31A, in which the circular arc shape has a curvature smaller than that of the inner periphery of the outer fastening ring 29. With the circular arc shape, it is possible to secure a large inner space of the inner fastening ring 31A.

Figure 45:
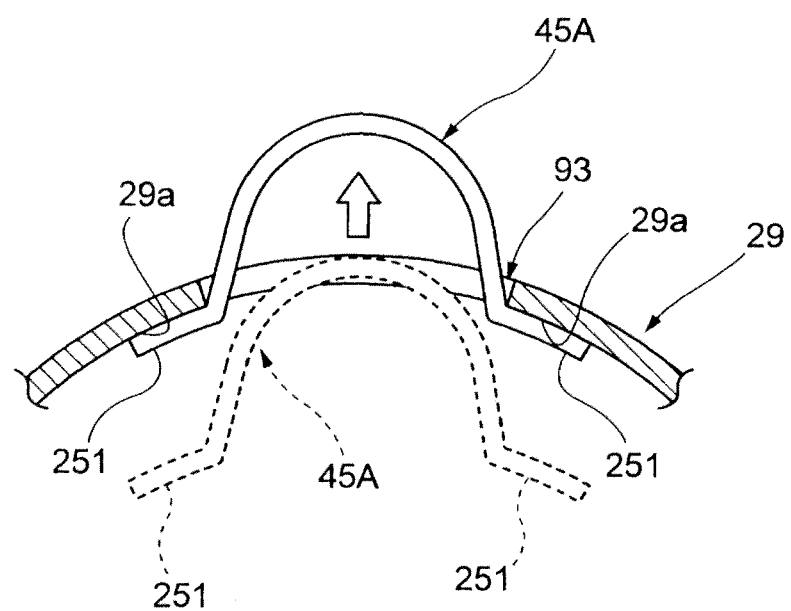
FIG. 45 is an explanatory view for describing the action of the flap parts illustrated in FIG. 44

The free ends 45a side of each of the flap parts 45A is formed with projection parts 251, 251 protruding to the opposite sides from the side surfaces of the flap part 45A. The projection parts 251, 251 abut against the edges 29a of the inner peripheries in the flap protruding holes 93 of the outer fastening ring 29 illustrated in FIG. 45, respectively, whereby the expansion extent of the each of the flap parts 45A, 45A is retained at a predetermined extent.

With this arrangement, the flap parts 45A, 45A retain the expansion extent thereof constant in the state where they protrude diametrically outward from the flap protruding holes 93. That is, a pair of the expanding flap parts 45A, 45A can be prevented from being opened excessively or insufficiently, and the expansion angle of the flap parts 45A, 45A can be reliably retained at the angle set at the time of design.

Although the example of configuration is provided with the flap parts 45A on the inner fastening ring 31, 31A, the outer fastening ring 29 may be provided with a flap part. In addition, it is possible to integrally form the inner fastening ring and the outer fastening ring with the same member, and to provide a flap part on the single integrally-formed fastening ring.

Figure 46:
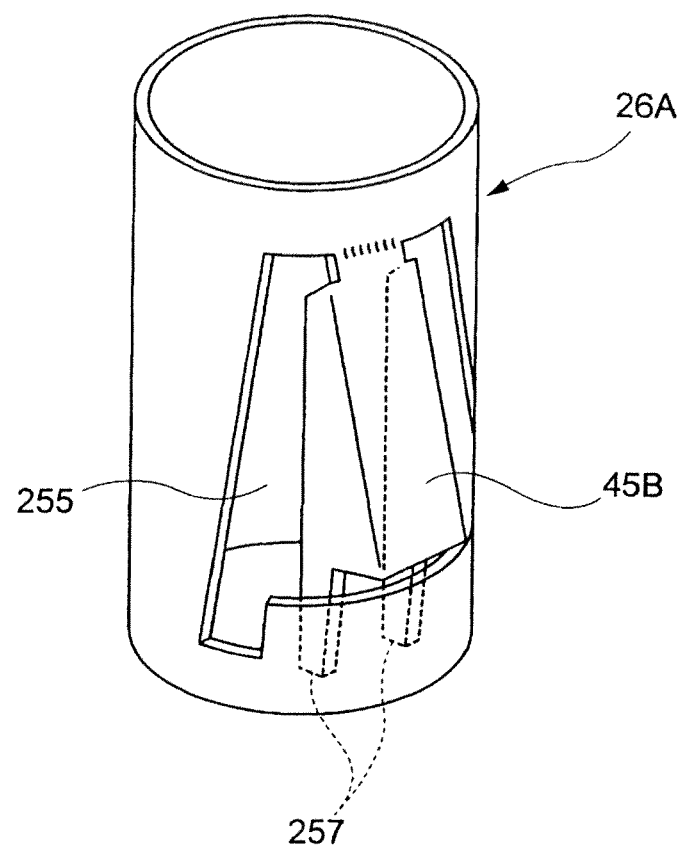
FIG. 46 is a perspective view schematically illustrating a construction in which a flap part is provided in a single fastening ring.
Figure 47A:
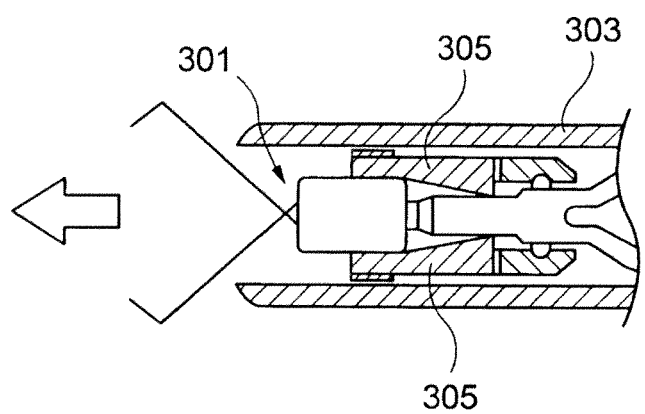
FIGS. 47A and 47B are explanatory views illustrating a conventional ligation device in a state where the clip unit is embedded in the sheath, and in astute where the clip unit is revealed to the outside of the sheath.
Figure 47B:
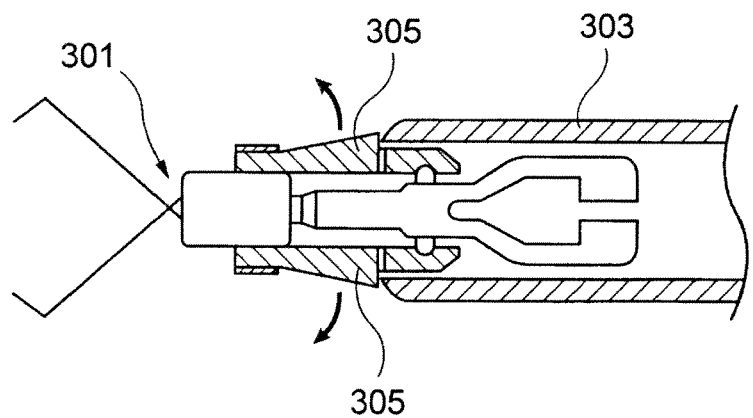

FIG. 46 is a perspective view schematically illustrating a construction in which a single fastening ring is provided with a flap part.

On the single fastening ring 26A, a flap part 45B is cantilevered. The flap part 45B is formed by cutting a part of the cylindrical fastening ring 26A. For that reason, an opening hole 255 is formed in a side of the fastening ring 26A. On the free end of the flap part 45B side, a pair of projection parts 257 and 257 extend, which are configured to abut against the inner periphery of the fastening ring 26A.

The flap part 45B is elastically biased in the diametrically outward direction of the fastening ring 26A in advance. As a result, the flap part 45B can retain the expansion extent at a predetermined extent in the state in which the projection parts 257, 257 abut against the inner periphery of the fastening ring 26A.

In addition, as described above, by forming the flap part with a thin metal plate, it is possible to reduce the thickness of the fastening ring itself, and to secure a large inner space. For this reason, the clip body and the hook may be directly connected within the fastening ring, no that it is not necessary to separately provide a connection member for connecting the clip body and the hook. Accordingly, it is possible to omit an operator's work for removing the connection member remaining in a ligation device whenever performing clipping, which may contribute to the speedup of a surgical operation. In addition, even if the connection member is used in the configuration, it is possible to miniaturize the flap part itself. Consequently, a clipping adaptive to an endoscope having a treatment instrument insertion channel of a smaller diameter can be realized.

As described above, the ligation device 100 is not limited to using it as a ligation device but may be converted into another treatment instrument for an endoscope that has a hook and an engagement claw part. In addition, it is possible to configure an endoscope system which enables a smooth endoscopic treatment by inserting the ligation device 100 through a treatment instrument inserting channel, through which a sheath member of an endoscope is inserted, and then introducing the ligation device 100 to the inside of a body cavity.

Like this, the present invention is not limited to the above-described exemplary embodiments. It is expected by the present invention that modifications and applications will be made by a person skilled in the art based on the disclosure of the specification and a well-known technology, and the modifications and applications are included in the scope to be protected.

As described above, the following items are disclosed in the specification.

(1) A clip unit for ligating a biological body includes: a clip body having a pair of arm parts; and a fastening ring arranged in an outside of the clip body, and configured to fasten the arm parts, in which: the fastening ring includes a flap part configured to expand diametrically outward from the fastening ring, and a flap retaining unit configured to retaining an expansion extent of the flap part at a given extent.

With this clip unit, the expansion extent of the flap part is securely retained at a predetermined extent by the flap retaining unit provided on the fastening ring. For this reason, the clip unit can always be correctly positioned in relation to a sheath member to axially coincide with the sheath member.

(2) In the clip unit according to ( ): the flap part is cantilevered on the fastening ring to extend along a longitudinal axis of the fastening ring, and a free end of the flap part is elastically biased to a diametrically outside of the fastening ring, and the flap retaining unit engages with the flap part, to restrain the expansion extent of the flap part.

With this clip unit, since the expansion extent of the flap part is controlled by the engagement of the fastening ring and the flap part, the expansion extent can be defined with excellent precision.

(3) In the clip unit according to (2): the fastening ring is configured by combining an inner fastening ring configured to support the flap part, and an outer fastening ring configured to cover the outside of the inner fastening ring and provided with a flap protruding hole, and the flap retaining unit retains the flap part in a state where the flap part protrudes diametrically outward from the flap protruding hole.

With this clip unit, the flap part is configured to expand and protrude from the flap protruding hole in the state where the inner fastening ring and the outer fastening ring are combined.

(4) In the clip unit according to (3): the cross-section of the flap part perpendicular to a longitudinal axis of the inner fastening ring is formed in a circular arc shape having a curvature smaller than that of an inner periphery of the outer fastening ring, and a flap locking hole is formed between a center of the circular arc and an end of the circular arc of the flap part, and the flap retaining unit includes a locking claw protruding from the flap protruding hole of the outer fastening ring toward an inside of the hole, and when inserted into the flap locking hole, abutting against a side surface of the flap locking hole.

With this clip unit, the expansion extent of the flap part is defined through the abutment of the side surface of the flap locking hole and the locking claw.

(5) In the clip unit according to (4): plural pairs of flap locking holes and locking claws which are engaged with each other.

With this clip unit, since the plural pairs of the flap locking holes and locking claws exist, it is possible to retain the flap part more stably.

(6) The clip unit according to (3) further includes: the flap part includes a projection part formed at the free end side thereof, and abutting against an edge of the flap protruding hole of the outer fastening ring.

With this clip unit, the expansion extent of the flap part is defined through the abutment of the edge of the flap protruding hole of the outer fastening ring and the projection part.

(7) In the clip unit according to (6): the flap part includes plural projection parts. With this clip unit, the flap part is retained more stably due to the existence of the plural projection parts.

(8) In the clip unit according to any one of (1) to (7): the flap part is provided a plural areas on the fastening ring.

With this clip unit, the flap part is adapted to be expanded at the plural areas on the fastening ring. For this reason, it is possible to obtain an effect of either stabilizing the posture or distributing force, for example when the flap parts abut against the front end of the sheath member, so that the clip unit can be stably supported.

(9) In the clip unit according to any one of (1) to (7): the flap part is installed to be capable of being embedded by being elastically deformed in an inside of the outer periphery of the fastening ring.

With this clip unit, the flap part may be embedded in the inside of the fastening ring. For this reason, the flap part does not interfere with the sheath member when the clip unit is accommodated in the sheath member.

(10) A ligation device includes: the clip unit according to any one of (1) to (9); a flexible elongated sheath member; a transmission member inserted into the sheath member to be capable of being reciprocated, and configured to transmit driving force to the clip unit connected to the front end of the transmission member; and a manipulation unit arranged on a base end side of the sheath member opposite to the clip unit, and configured to transmit the driving force to the transmission member.

With this ligation device, it is possible to obtain an effect of either stabilizing the posture or distributing force, for example when the flap parts abut against the front end of the sheath member, so that the clip unit can be stably supported in the state in which the clip unit axially coincide with the sheath member at the front end of the sheath member. Accordingly, a smooth and certain ligation action can be obtained.

(11) The ligation device according to (10): the expansion extent of the flap part is an expansion extent that makes the flap part abut against a front end of the sheath member when the transmission member is pulled into the sheath member.

With this ligation device, the flap part surely abuts against the end of the sheath member, thereby being positioned.

What is claimed is:

1. A clip unit for lighting a biological body comprising:
a clip body having a pair of arm parts; and
a fastening ring arranged in an outside of the clip body, and configured to fasten the arm parts, wherein:
the fastening ring includes a flap part configured to expand diametrically outward from the fastening ring, and a flap retaining unit configured to retain the flap part, and
the flap retaining unit engages with the flap part, to restrain the flap part from expanding diametrically outward from the fastening ring
wherein the flap part is cantilevered on a ring part of the fastening ring to extend along a longitudinal axis of the fastening ring, and the flap part is elastically biased diametrically outward from the fastening ring,
wherein the fastening ring is configured by combining an inner fastening ring configured to support the flap part, and an outer fastening ring configured to cover the outside of the inner fastening ring and provided with a flap protruding hold which is formed on a peripheral surface of the outer fastening ring and extends along the longitudinal axis of the fastening ring and the flap retaining unit retains the flap part in a state where the flap part protrudes diametrically outward from the flap protruding hole.

2. The clip unit according to claim 1, wherein:
the cross-section of the flap part perpendicular to a longitudinal axis of the inner fastening ring is formed in a circular arc shape having a curvature smaller than that of an inner periphery of the outer fastening ring, and
a flap locking hole is formed on the inner fastening ring between a center of the circular arc shape and an end of the circular arc of the flap part, and
the flap retaining unit includes a locking claw protruding from the flap protruding hole of the outer fastening ring toward an inside of the hole, and when inserted into the flap locking hole, abutting against a side surface of the flap locking hole.

3. The clip unit according to claim 2, wherein:
another flap locking hole is formed in the flap part, and
another locking claw engaging with said another flap locking hole is formed in the flap retaining unit.

4. The clip unit according to claim 1, further comprising:
the flap part includes a projection part formed at the free end side thereof, and abutting against an edge of the flap protruding hole of the outer fastening ring.

5. The clip unit according to claim 4, wherein:
the flap part includes plural projection parts.

6. The clip unit according to claim 1, wherein:
another flap part is provided on the ring part of the fastening ring.

7. The clip unit according to claim 1, wherein:
the flap part is installed to be capable of being embedded by being elastically deformed in an inside of the outer periphery of the fastening ring.

8. A ligation device comprising:
the clip unit according to claim 7;
a flexible elongated sheath member;
a transmission member inserted into the sheath member to be capable of being reciprocated, and configured to transmit driving force to the clip unit connected to the front end of the transmission member; and
a manipulation unit arranged on a base end side of the sheath member opposite to the clip unit, and configured to transmit the driving force to the transmission member.

9. The ligation device according to claim 8, wherein:
the flap part is configured to abut against a front end of the sheath member when the transmission member is pulled into the sheath member.

10. The clip unit according to claim 1, wherein the flap part has a surface abutting against an inner peripheral surface of the fastening ring.

11. The clip unit according to claim 1, wherein the flap part comprises a thin plate.

12. The clip unit according to claim 1, wherein the clip body is directly connected within the fastening ring.

13. The clip unit according to claim 1, wherein the flap part comprises:
a circular arc shape in a diametrical cross-section perpendicular to the axial direction; and
a bulge part disposed at an axially central area thereof,
wherein a length of the circular arc shape in the diametrical cross-section is increased at the bulge part.

14. The clip unit according to claim 1, wherein the outer fastening ring includes:
a cylindrical section;
a constricted spot formed by reducing a diameter of the cylindrical section in a vicinity of a front end of the cylindrical section; and
a taper section extending from the constricted spot such that a diameter of the taper section is increased towards a front end side.

15. The clip unit according to claim 14, wherein the outer fastening ring and the inner fastening ring are engaged with each other by inserting the inner fastening ring into the cylindrical section of the outer fastening ring in such a manner that a ring part side is positioned at a forefront.

\* \* \* \* \*